United States Patent
Buchmueller et al.

(10) Patent No.: US 10,053,236 B1
(45) Date of Patent: Aug. 21, 2018

(54) AUTOMATED AERIAL VEHICLE INSPECTIONS

(71) Applicant: Amazon Technologies, Inc., Seattle, WA (US)

(72) Inventors: Daniel Buchmueller, Seattle, WA (US); Samuel Sperindeo, Cambridge (GB)

(73) Assignee: Amazon Technologies, Inc., Seattle, WA (US)

( * ) Notice: Subject to any disclaimer, the term of this patent is extended or adjusted under 35 U.S.C. 154(b) by 123 days.

(21) Appl. No.: 15/083,161

(22) Filed: Mar. 28, 2016

(51) Int. Cl.
| | |
|---|---|
| *B64F 5/00* | (2017.01) |
| *G07C 5/00* | (2006.01) |
| *G07C 5/08* | (2006.01) |
| *G01L 1/16* | (2006.01) |
| *G01N 29/04* | (2006.01) |
| *G06K 9/62* | (2006.01) |

(52) U.S. Cl.
CPC ............. *B64F 5/0045* (2013.01); *G01L 1/16* (2013.01); *G01N 29/04* (2013.01); *G06K 9/6201* (2013.01); *G06K 9/6262* (2013.01); *G07C 5/006* (2013.01); *G07C 5/0808* (2013.01); *G01N 2291/023* (2013.01); *G01N 2291/0289* (2013.01)

(58) Field of Classification Search
None
See application file for complete search history.

(56) References Cited

U.S. PATENT DOCUMENTS

| | | | |
|---|---|---|---|
| 2010/0235037 A1* | 9/2010 | Vian ..................... | G07C 5/008 701/31.4 |
| 2012/0250010 A1* | 10/2012 | Hannay ................ | G01N 21/952 356/237.1 |
| 2014/0067164 A1* | 3/2014 | Papadopoulos ........ | B64G 1/002 701/3 |

(Continued)

OTHER PUBLICATIONS

A. Krizhevsky, I. Sutskever, and G. E. Hinton. Imagenet classification with deep convolutional neural networks. NIPS 12 Proceedings of the 25th Int'l Conference on Neural Information Processing Systems (vol. 1), Lake Tahoe, Nevada, pp. 1097-1105, 2012.

(Continued)

*Primary Examiner* — Bao Long T Nguyen
*Assistant Examiner* — Kelly D Williams
(74) *Attorney, Agent, or Firm* — Athorus, PLLC

(57) ABSTRACT

Automated inspections of aerial vehicles may be performed using imaging devices, microphones or other sensors. Between phases of operation, the aerial vehicle may be instructed to perform a plurality of testing evolutions, e.g., in a sequence, at a testing facility, and data may be captured during the evolutions by sensors provided on the aerial vehicle and by ground-based sensors at the testing facility. The imaging and acoustic data may be processed to determine whether any vibrations or radiated noises during the evolutions are consistent with faults or discrepancies of the aerial vehicle such as microfractures, corrosions or fatigue. If no faults or discrepancies are detected, the aerial vehicle may be returned to service without delay. If any faults or (Continued)

discrepancies are detected, however, then the aerial vehicle may be subjected to maintenance, repairs or further manual or visual inspections.

25 Claims, 17 Drawing Sheets

(56) References Cited

U.S. PATENT DOCUMENTS

| | | | | |
|---|---|---|---|---|
| 2015/0336671 | A1* | 11/2015 | Winn | B64C 39/024 701/3 |
| 2016/0003954 | A1* | 1/2016 | Broussard, III | G01V 1/003 244/76 R |
| 2016/0093124 | A1* | 3/2016 | Shi | G07C 5/0808 701/2 |
| 2016/0264262 | A1* | 9/2016 | Colin | B25J 5/007 |
| 2016/0376031 | A1* | 12/2016 | Michalski | B64F 1/36 701/15 |

OTHER PUBLICATIONS

R. Radford, L. Metz, and S. Chintala. Unsupervised Representation Learning with Deep Convolutional Generative Adversarial Networks. Submitted as Conference Paper for ICLR 2016, San Juan, Puerto Rico, May 2-4, 2016.
A. Shrivastava, T. Pfister, O. Tuzel, J. Susskind, W. Wang, and R. Webb. Learning from Simulated and Unsupervised Images through Adversarial Training. Submitted Nov. 15, 2016, for oral presentation at Conference on Computer Vision and Pattern Recognition (CVPR 2017), Honolulu, Hawaii; presented at CVPR 2017 on Jul. 23, 2017.
B. Zhou, A. Khosla, A. Lapedriza, A. Oliva, and A. Torralba. Learning Deep Features for Discriminative Localization. In Proceedings of the IEEE Conference on Computer Vision and Pattern Recognition (CVPR 2016), Las Vegas, Nevada, pp. 2921-2929, IEEE 2016.
D. Soukup and R. Huber-Mörk. Convolutional Neural Networks for Steel Surface Defect Detection from Photometric Stereo Images, pp. 668-677. Advances in Visual Computing, 10th Int'l Symposium (ISVC 2014), Las Vegas, Nevada, Dec. 8-10, 2014. Springer International Publishing, Switzerland, 2014 (LNCS 8887).
D. Kingma and J. Ba. Adam: A Method for Stochastic Optimization, The Hebrew University of Jerusalem, Advanced Seminarin Deep Learning, Oct. 18, 2015.
D. Kingma and J. Ba. Adam: A method for stochastic optimization. Published at the 3rd International Conference for Learning Representations (ICLR 2015), San Diego, May 9, 2015.
D. Martin. A Practical Guide to Machine Vision Lighting, Advanced Illumination, Rochester, Vt., Feb. 2012.
D. Mery and M.A. Berti. Automatic Detection of Welding Defects Using Texture Features. Insight-Non-Destructive Testing and Condition Monitoring, 45(10):676-681, 2003. Presented at Int'l Symposium on Computed Tomography and Image Processing for Industrial Radiology, Berlin, Germany, Jun. 23-25, 2003.
D. Sammons, W.P. Winfree, E. Burke, and S. Ji. Segmenting delaminations in carbon fiber reinforced polymer composite CT using convolutional neural networks. AIP Conference Proceedings, vol. 1706, p. 110014. American Institute of Physics, AIP Publishing, 2016.
D. Vernon. Machine Vision: Automated Visual Inspection and Robot Vision. Automatica, vol. 30, No. 4, pp. 731-732 (1994), Elsevier Science, Ltd., Great Britain.

D. Wang, A. Khosla, R. Gargeya, H. Irshad, and A. H. Beck. Deep Learning for Identifying Metastatic Breast Cancer. Computer Research Repository (CoRR), Jun. 18, 2016.
G. Wang and T. Liao. Automatic identification of different types of welding defects in radiographic images. NDT&E International, 35(8):519-528 (2002), Elsevier Science Ltd., Great Britain.
H. Raafat and S. Taboun. An Integrated Robotic and Machine Vision System for Surface Flaw Detection and Classification. Computers & Industrial Engineering, Elsevier Science Ltd., Great Britain, 30(1):27-40, 1996.
I. Goodfellow, J. Pouget-Abadie, M. Mirza, B. Xu, D. Warde-Farley, S. Ozair, A. Courville, and Y. Ben-gio. Generative adversarial nets. Advances in Neural Information Processing Systems (NIPS 2014), pp. 2672-2680, 2014.
J. Deng, W. Dong, R. Socher, L.-J. Li, K. Li, and L. Fei-Fei. Imagenet: A large-scale hierarchical image database. In IEEE Conference on Computer Vision and Pattern Recognition, 2009 (CVPR 2009), Miami, Florida, pp. 248-255. IEEE 2009.
J. Long, E. Shelhamer, and T. Darrell. Fully Convolutional Networks for Semantic Segmentation. In Proceedings of the IEEE Conference on Computer Vision and Pattern Recognition (CVPR 2015), Boston, Mass., pp. 3431-3440, IEEE 2015.
J. Masci, U. Meier, D. Ciresan, J. Schmidhuber, and G. Fricout. Steel Defect Classification with Max-Pooling Convolutional Neural Networks. The 2012 International Joint Conference on Neural Networks (IJCNN), Brisbane, Australia, pp. 1-6. IEEE, Jun. 2012.
J. Redmon, S. Divvala, R. Girshick, and k Farhadi. You Only Look Once: Unified, Real-Time Object Detection. Jroceedings of the 2016 IEEE Conference on Computer Vision and Pattern Recognition (CVPR 2016), Las Vegas, Nevada, pp. 779-788, IEEE 2016.
D. Mery and M.A. Berti. Automatic Detection of Welding Defects Using Texture Features. Insight—Non-Destructive Testing and Condition Monitoring, 45(10):676-681, 2003. Presented at Int'l Symposium on Computed Tomography and Image Processing for Industrial Radiology, Berlin, Germany, Jun. 23-25, 2003.
K. Simonyan and A. Zisserman. Very Deep Convolutional Networks for Large-Scale Image Recognition. Submitted Sep. 4, 2014, for publication at 3d Int'l Conference on Learning Representations (ICLR 2015), San Diego, California. Presented May 7-9, 2015.
N. Srivastava, G. E. Hinton, A. Krizhevsky, I. Sutskever, and R. Salakhutdinov. Dropout: A Simple Way to Prevent Neural Networks from Overfilling. Journal of Machine Learning Research, 15(1):1929-1958, 2014.
S. Ioffe and C. Szegedy. Batch normalization: Accelerating deep network training by reducing internal covariate shift. In Proceedings of the 32nd International Conference on Machine Learning, Lille, France, pp. 448-456, 2015.
T.-Y. Lin, A. RoyChowdhury, and S. Maji. Bilinear CNN Models for Fine-Grained Visual Recognition. Proceedings of the 2015 IEEE International Conference on Computer Vision (ICCV), Santiago, Chile, pp. 1449-1457, IEEE 2015.
T.-Y. Lin, P. Goyal, R. Girshick, K. He, and P. Dollar. Focal Loss for Dense Object Detection. IEEE International Conference on Computer Vision (2017), pp. 966-974, IEEE 2017.
Y. Gao, O. Beijbom, N. Zhang, and T. Darrell. Compact bilinear pooling. In Proceedings of the IEEE Conference on Computer Vision and Pattern Recognition (CVPR 2016), Las Vegas, Nevada, pp. 317-326, IEEE 2016.
Y. Liu, K. Gadepalli, M. Norouzi, G.E. Dahl, T. Kohlberger, A. Boyko, S. Venugopalan, A. Timofeev, P.Q. Nelson, G.S. Corrado, et al. Detecting Cancer Metastases on Gigapixel Pathology Images. Google Research, Mar. 8, 2017.

* cited by examiner

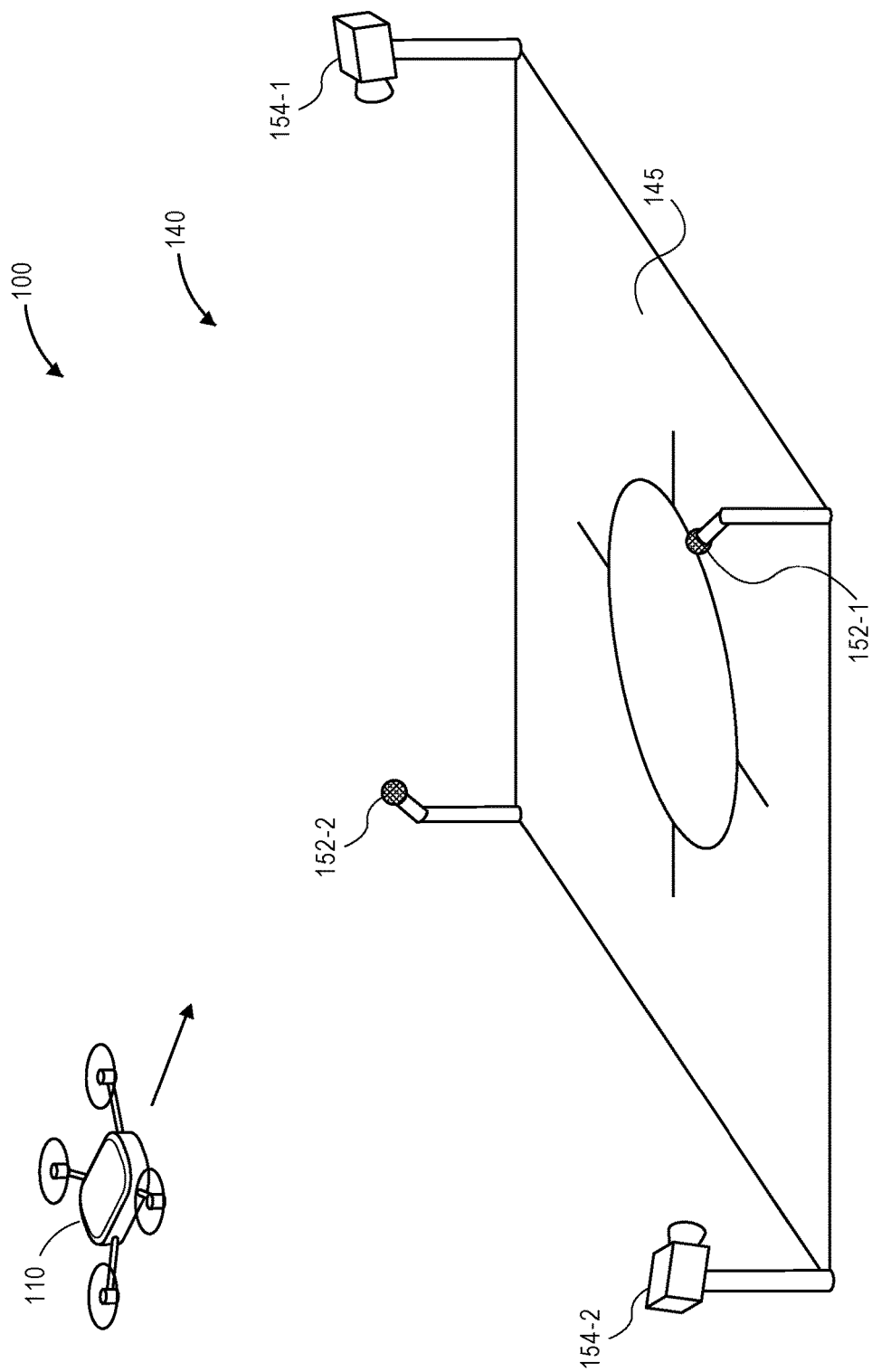

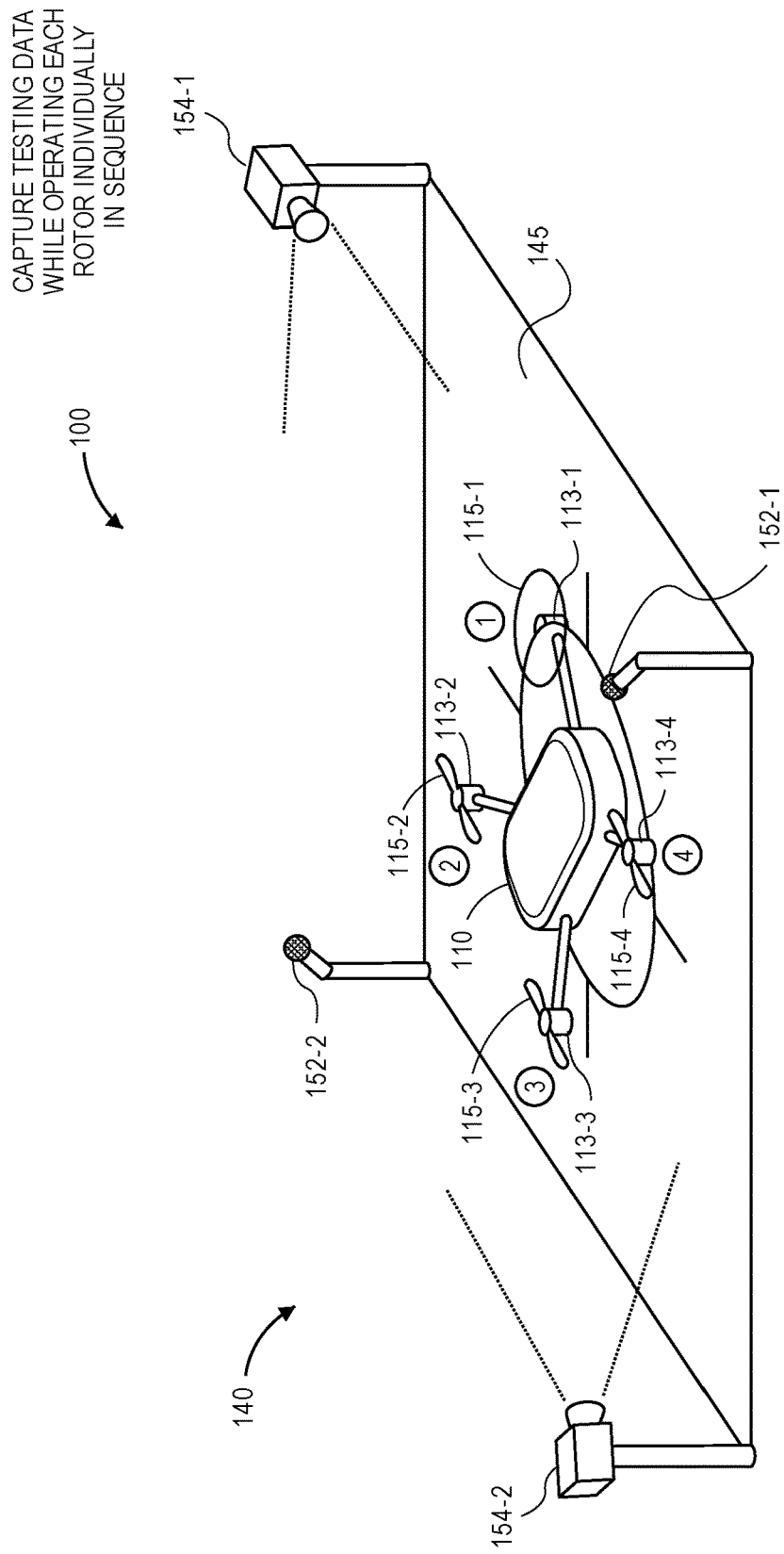

AUTOMATED AERIAL VEHICLE INSPECTIONS

BACKGROUND

Aerial vehicles such as airplanes or helicopters are commonly used to transport people or cargo from an origin to a destination by air. Aerial vehicles may be delicate machines that are formed from lightweight metals, plastics or composites and equipped with motors, rotors or turbofans that are designed to meet or exceed a number of operational constraints or requirements such as speed, altitude or lift. For example, many unmanned aerial vehicles (UAVs, or drones) are built from molded plastic frames and outfitted with electric motors powered by onboard batteries that permit the vehicles to conduct lifting or thrusting operations, while larger aerial vehicles such as jumbo jets feature aluminum, titanium or carbon fiber frames and skins and are equipped with petroleum-powered jet engines capable of generating tens of thousands of pounds-force.

During flight operations, an aerial vehicle may be subject to intense vibrations or oscillations due to thrusting or lifting forces acting on the aerial vehicle, environmental conditions in an area where the aerial vehicle operates or has operated, shocks or impacts from contact with one or more other objects, or from any other sources. Therefore, from time to time, such as after a nominal or predetermined number of operating hours or missions, aerial vehicles are commonly taken out of service for a number of manual or visual inspections. Such inspections are intended to determine whether the strength and integrity of the various components of the aerial vehicle remain sufficient for normal operations. For example, an aerial vehicle may be searched for microfractures, cracks, loosened or broken fasteners, corrosions, fatigue, or evidence of other physical manifestations of stress or strain.

Performing manual or visual inspections typically requires taking an aerial vehicle out of service for extended durations, however. For example, depending on a size of an aerial vehicle, or a length of time since a most recent inspection, a typical inspection of the aerial vehicle may require tens or hundreds of man-hours in order to be completed. Even where a manual or visual inspection results in a determination that the integrity of the aerial vehicle is sound and that the aerial vehicle is operating in a safe and satisfactory manner, the aerial vehicle must still be taken out of service in order to arrive at that determination. Conversely, where an inspection regime calls for manual or visual evaluations to be conducted periodically, e.g., after a predetermined number of hours have lapsed or missions have been completed, such evaluations are unable to determine when an operational issue arises between such periodic inspections, and implementing a remedy for the operational issue is necessarily delayed. Every hour in which an aerial vehicle is out-of-service is an hour in which the aerial vehicle is not providing value.

BRIEF DESCRIPTION OF THE DRAWINGS

FIGS. 1A through 1D are views of aspects of one system for automated aerial vehicle inspections in accordance with embodiments of the present disclosure.

DETAILED DESCRIPTION

Figure 1B:
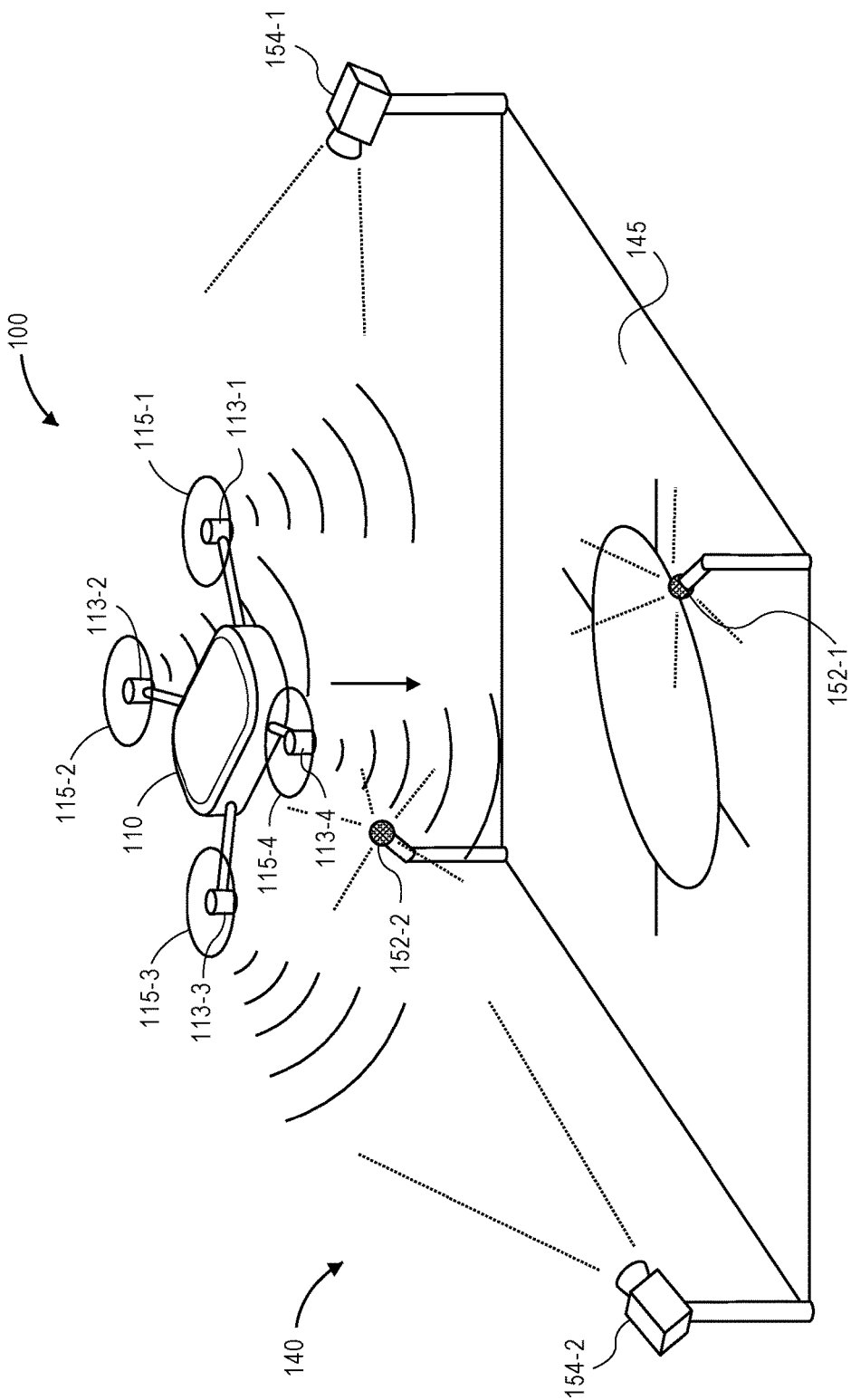

As is set forth in greater detail below, the present disclosure is directed to automatically performing inspections of an aerial vehicle using data captured from the aerial vehicle by one or more sensors provided in a ground-based facility or aboard the aerial vehicle, and using such data to determine whether the aerial vehicle requires maintenance, or whether the aerial vehicle may be used in further operations. For example, when an aerial vehicle is initially prepared for operations, a set of data may be captured from the aerial vehicle using not only sensors provided on the aerial vehicle, such as gyroscopes, accelerometers, magnetometers, imaging devices or microphones, but also one or more other sensors that are provided at a landing facility or range. The set of data may be captured using sensors provided on the aerial vehicle or ground-based sensors as the aerial vehicle is operated according to a predetermined testing sequence, e.g., by operating one or more powered elements such as motors, rotors or control surfaces. Operating the powered elements independently or in tandem, or in any combinations, causes a unique vibrational excitation of the aerial vehicle, and the manner in which the aerial vehicle responds to the vibrational excitations may be captured using the one or more sensors. For example, the predetermined testing sequence may call for operating each of the motors individually or collectively, or in one or more combinations, and at operating speeds that may be varied gradually or suddenly. Likewise, any control surfaces or other structural components may also be operated individually or collectively, or in any combinations, within predetermined ranges or limits associated with such surfaces or components. Information or data captured during the operation of the powered elements may then be analyzed in order to derive one or more signatures reflective of the safety or sufficiency of operation of the aerial vehicle, or the integrity of one or more components thereof.

After an aerial vehicle has completed a mission, or when the aerial vehicle is otherwise between phases of operation, the aerial vehicle may again be operated according to the predetermined testing sequence, e.g., as each of the powered elements of the aerial vehicle is operated independently or in tandem, or in any combinations, and another set of data may be captured during the operation. Such data may be used along with operational data recorded during the mission to determine whether the aerial vehicle is operating safely and sufficiently, and may thus be cleared for its next mission, or whether the aerial vehicle requires maintenance, repairs or further inspection, and is to be blocked from its next mission. Thus, based on data captured using both onboard sensors and ground-based sensors, whether an aerial vehicle requires maintenance, repairs or further inspections may be determined more efficiently than according to traditional methods, thereby enabling aerial vehicles for which no maintenance, repairs or further inspections are required to be returned to service without further delay, while ensuring that actual or emerging faults or discrepancies in such aerial vehicles are diagnosed and corrected as quickly as possible.

Referring to FIGS. 1A through 1D, aspects of one system 100 for automated aerial vehicle inspections is shown. The system 100 includes an aerial vehicle 110 and a testing facility 140. The aerial vehicle 110 includes a plurality of motors 113-1, 113-2, 113-3, 113-4 and a plurality of rotors 115-1, 115-2, 115-3, and 115-4. The testing facility 140 includes a landing pad 145, and a plurality of sensors aligned within an operating range of the landing pad 145, including a pair of acoustic sensors (e.g., microphones) 152-1, 152-2 and a pair of imaging devices 154-1, 154-2 (e.g., digital cameras). Each of the acoustic sensors 152-1, 152-2 and imaging devices 154-1, 154-2 mounted in association with the landing pad 145, e.g., atop one or more stanchions, posts or other structures, and aligned to capture information or data from one or more aerial vehicles returning to the landing pad 145 or departing from the landing pad 145. Alternatively, one or more of the sensors provided about the landing pad 145 may be mobile in nature, e.g., provided on a vehicle or robot that may enter within an operating range of the landing pad 145 to capture information or data regarding the aerial vehicle 110, and depart from the operating range of the landing pad 145 after the information or data has been captured, such as to evaluate another aerial vehicle on a different landing pad. In addition to imaging devices and acoustic sensors, the testing facility may further include any other type or form of other sensors (not shown) for capturing information or data from vehicles at the landing pad 145. The testing facility 140 and/or the landing pad 145 may be associated with any type or form of other structures or facilities (not shown) associated with missions that are to be performed by one or more aerial vehicles, such as the aerial vehicle 110, including but not limited to airborne delivery or surveillance operations.

As is shown in FIGS. 1A and 1B, the aerial vehicle 110 is returning to the testing facility 140, e.g., following a completion of a mission. As is shown in FIG. 1B, each of the motors 113-1, 113-2, 113-3, 113-4 is rotating each of the rotors 115-1, 115-2, 115-3, 115-4 under power as the aerial vehicle 110 prepares to land on the landing pad 145.

As is shown in FIG. 1C, after the aerial vehicle 110 has arrived at the testing facility 140, the aerial vehicle 110 may subjected to a sequence of any number of automatic testing evolutions within the audible ranges of the acoustic sensors 152-1, 152-2 and the fields of view of the imaging devices 154-1, 154-2. For example, as is shown in FIG. 1C, each of the motors 113-1, 113-2, 113-3, 113-4 may be operated independently and in series, such that acoustic and imaging data may be captured using the acoustic sensors 152-1, 152-2 and the imaging devices 154-1, 154-2. Alternatively, where the aerial vehicle 110 includes one or more control surfaces, e.g., one or more rudders, elevators, stabilizers, spoilers, ailerons, flaps or slats, or other operable components (such as extendible or retractable landing gear or the like), such other surfaces or other components may also be operated in accordance with the sequence of testing evolutions.

Figure 1D:
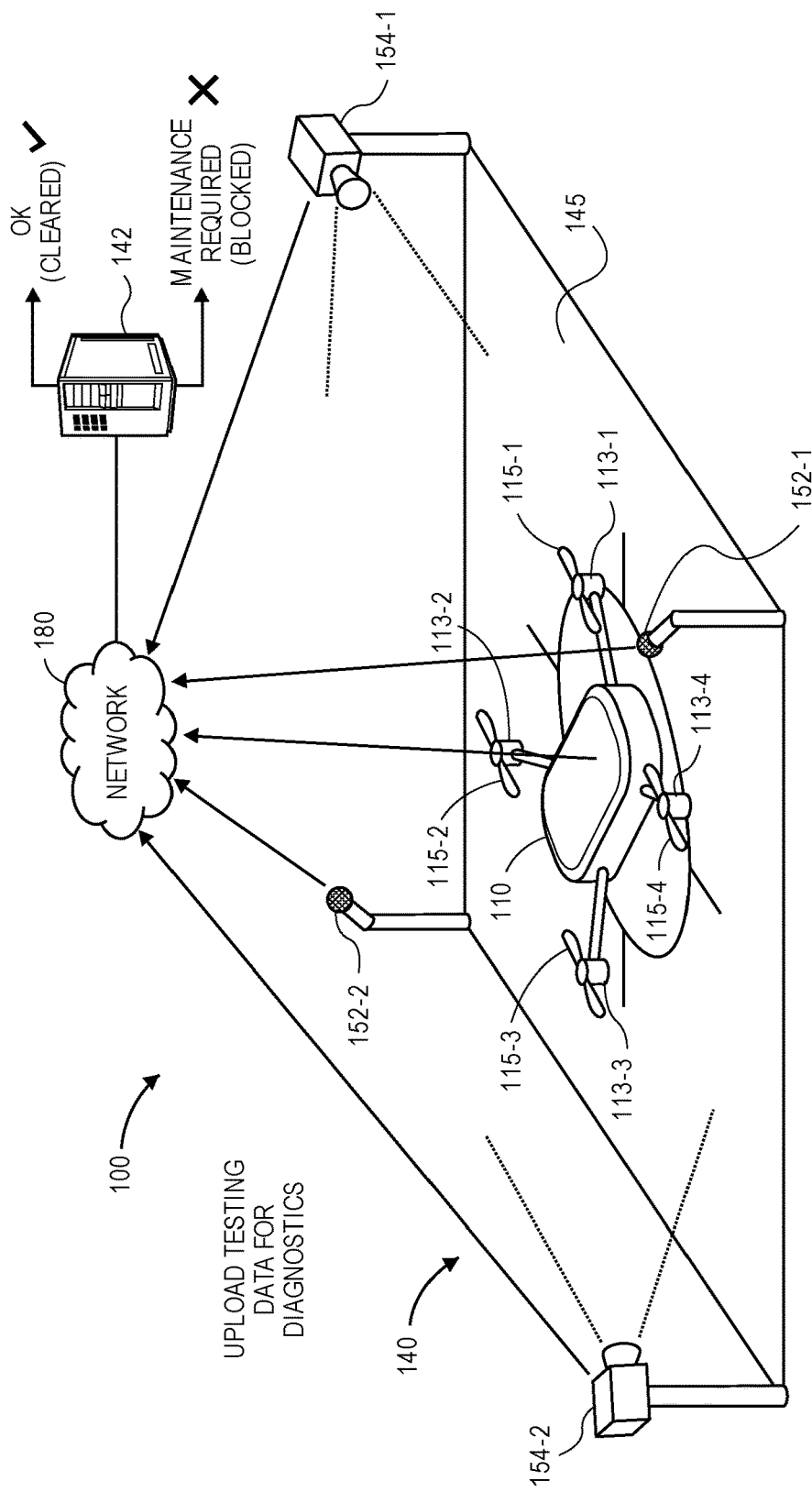

As is shown in FIG. 1D, after the sequence of testing evolutions is completed, either in whole or in part, information or data captured by sensors provided onboard the aerial vehicle 110 during prior operations (e.g., one or more missions that preceded the sequence of testing evolutions) and information or data captured by both onboard sensors and ground-based sensors during the sequence of testing evolutions may be uploaded to one or more servers 142 associated with the testing facility 140, e.g., over a network 180, by wireless or wired connections. The servers 142 may determine whether the aerial vehicle 110 requires maintenance, repairs or further inspections based on a modal analysis of acoustic data or imaging data captured using the acoustic sensors 152-1, 152-2 or the imaging devices 154-1, 154-2, or any data captured by other sensors provided aboard the aerial vehicle 110 or at the testing facility 140 (not shown).

For example, the servers 142 may generate a signature, a fingerprint or another set of data representative of activity embodied in the respective sounds or images, captured during operations of each of the powered elements individually or in the aggregate. The signature, fingerprint or other set of data may be compared to baseline data for the aerial vehicle 110, or predicted data regarding the operation of the aerial vehicle 110, e.g., to another signature, fingerprint or other set of data representative of activity that was previously obtained, according to one or more machine learning algorithms or techniques. Where the observed acoustic data or imaging data is determined to be consistent with expectations determined based on the baseline data or predicted data, e.g., based on a comparison of signatures, fingerprints or other sets of data, the aerial vehicle 110 may be understood to not require any maintenance, repairs or further inspections of any type of form, and may depart on another mission momentarily. Where the observed acoustic data or imaging data is not consistent with such expectations, however, maintenance, repairs or further inspections may be conducted in order to determine a cause of any discrepancies.

Accordingly, the systems and methods of the present disclosure may be utilized to automate and regulate the performance of inspections, maintenance and repairs on aerial vehicles. In particular, such systems and methods may replace traditional periodic manual or visual inspections with automatic inspections that are conducted based on information or data captured using sensors onboard an aerial vehicle, and ground-based sensors at a landing area or testing facility. The automatic inspections may be conducted using acoustic data or imaging data captured by acoustic sensors or imaging devices, as well as any other type or form of relevant information or data captured using gyroscopes, accelerometers, magnetometers or other sensors provided on the aerial vehicle or at the testing facility. For example, an initial signature (or fingerprint, or other set of data) may be determined for an aerial vehicle based on an analysis of information or data captured during an initial execution of a testing sequence that calls for the operation of each of a plurality of powered elements onboard the aerial vehicle within operating ranges of sensors (e.g., within an acoustic range of one or more acoustic sensors, within a field of view of one or more imaging devices, or within operating ranges of any other sensors). In some embodiments, the initial signature may be defined based on a modal analysis of the information or data captured during the initial execution of the testing sequence, and may include a representation of an initial spectral density of accelerations, e.g., linear and/or angular, or vibrations measured during the initial execution of the testing sequence by sensors provided on the aerial vehicle or at the testing facility.

Subsequently, e.g., when the aerial vehicle returns from performing a mission, or when the aerial vehicle is between two phases of operation, the aerial vehicle may execute the testing sequence again within the operating ranges of such sensors. A subsequent signature (or fingerprint, or other set of data) may be determined based on a subsequent analysis of information or data captured during the subsequent execution of the testing sequence, and compared to initial signature determined based on the information or data captured during the initial execution of the testing sequence. Based on the subsequent signature, or a comparison of the subsequent signature to the initial signature, a determination may be made as to whether the aerial vehicle is experiencing any structural deficiencies (e.g., microfractures, cracks, loosened or broken fasteners, corrosions, fatigue, other physical manifestations of stress or strain), or whether maintenance, repairs or further inspections may be required. In some embodiments, the subsequent signature may, like the initial signature, be defined based on a modal analysis of the information or data captured during the subsequent execution of the testing sequence, and may include a representation of a subsequent spectral density of accelerations, e.g., linear and/or angular, or vibrations measured during the subsequent execution of the testing sequence by sensors provided on the aerial vehicle or at the testing facility. Whether the aerial vehicle is experiencing structural deficiencies, or requires any maintenance, repairs or further inspections, may be determined based at least in part on a comparison of the spectral densities of accelerations or vibrations measured during the initial and subsequent executions of the testing sequence. Additionally, the testing sequence may be performed again and again, as necessary, e.g., after each mission performed by the aerial vehicle, between any two phases of operation of the aerial vehicle, or on a predetermined schedule.

Sound is generated when motion or vibration of an object results in a pressure change in a medium, such as air, surrounding the object. For example, when such motion or vibration occurs, the densities of the molecules of the medium within a vicinity of the object are subjected to alternating periods of condensation and rarefaction, resulting in contractions and expansions of such molecules, which causes the issuance of a sound wave that may travel at speeds of approximately three hundred forty-three meters per second (343 m/s) in dry air. The intensity of sounds is commonly determined as a sound pressure level (or sound level), and is measured in logarithmic units called decibels (dB).

In industrial applications, noise is typically generated as mechanical noise, fluid noise or electromagnetic noise. Mechanical noise typically results when a solid vibrating surface, e.g., a driven surface, or a surface in contact with one or linkages or prime movers, emits sound power that is a function of a density of a medium, the speed of sound within the medium, the vibrating area, the mean square vibrating velocity of the medium to a vibrating area and a mean square vibrating velocity, and the radiation efficiency of the material. Fluid noise generated by turbulent flow is generally proportional to multiple orders of flow velocity, e.g., six to eight powers greater than the velocity of the turbulent flow, while sound power generated by rotating fans is determined according to a function of flow rate and static pressure. In electric motors, noise may be generated due to airflow at inlets and outlets of cooling fans, bearing or casing vibrations, motor balancing shaft misalignment or improper motor mountings.

With regard to a frequency spectrum, emitted sounds generally fall into one of two categories. Sounds having energies that are typically concentrated or centered around discrete frequencies are classified as narrowband noise, or narrowband tonals, and are commonly periodic in nature. Narrowband noise is commonly encountered in many industrial applications. For example, many rotating machines such as internal combustion engines, compressors, vacuum pumps or other rotating machines may inherently vibrate at frequencies associated with their angular velocities, as well as electric power transformers that generate large magnetic fields and thereby vibrate at harmonics of line frequencies. Conversely, sounds having energies that are distributed across bands of frequencies are classified as broadband noise. Additionally, some machines or sound sources may emit sounds that are combinations of narrowband noise and broadband noise, e.g., sounds that have component energy levels that are concentrated about one or more discrete frequencies and also across entire frequency spectra.

Aerial vehicles are typically evaluated from time to time for failures or deficiencies in materials and components. Because aerial vehicles commonly radiate noise and/or other vibrations in response to thrust or lift forces, flow conditions, impacts or other adverse events, aerial vehicles must be routinely inspected to properly assess risks of failure of a specific component, of the aerial vehicle as a whole, or of aerial vehicles in a fleet. Whether conditions or deficiencies such as microfractures, cracks, fractured fasteners, corrosions, fatigue, or other adverse conditions exist on an aerial vehicle may be assessed with respect to structural components, control surfaces, motors or rotors or appurtenances such as landing gear. In particular, structural joints on aerial vehicles, e.g., concentrated locations where loads and stresses are transferred from one component to another, such as by fasteners, are particularly susceptible to cracks or other indicia of fatigue. For example, relative movement between structural details and fasteners, as well as stress concentrations, may cause, enable or exacerbate microfractures, corrosions or cracking within such fasteners or structural details, such as fuselage skins or other components. If left untreated, microfractures, corrosions or cracking may lead to serious structural failures of the structural details or fasteners, or the aerial vehicle as a whole.

The systems and methods of the present disclosure are directed to performing inspections of aerial vehicles on an automatic and continuous basis while transitioning between different phases of an aerial vehicle's operation. The systems and methods disclosed herein enable traditional, periodic and/or manual inspections of aerial vehicles to be augmented or replaced with continuous inspections that are performed using information or data gathered by both onboard sensors and also ground-based sensors. For example, an aerial vehicle may be outfitted with a number of sensors for aiding in flight control or guidance, including but not limited to one or more Global Positioning System (GPS) sensors, accelerometers, gyroscopes, magnetometers, acoustic sensors or imaging devices. A ground-based testing facility may further include stationary or mobile sensors, including one or more high quality acoustic sensors (e.g., high fidelity microphones), one or more imaging devices (e.g., high frame rate cameras), or any other sensors such as gyroscopes, accelerometers, magnetometers or other sensors. The integrity of the aerial vehicle may be evaluated using information or data captured using such sensors, e.g., to determine an aerodynamic signature of an aerial vehicle, or detect any failures in blades, bearings, surfaces or rotating components that lead to operational inconsistencies that deviate from typical behavior, or otherwise evaluate the integrity of such components based on the information or data. In some implementations, surfaces or components may be lined or covered with reflective materials or surfaces. Natural or artificial light may be directed to such materials or surfaces for enhancing the visibility of such materials or surfaces and improving the manner in which information or data regarding their operability is captured.

The systems and methods disclosed herein may determine whether aerial vehicles require maintenance based on information or data captured during phases of operation, and also between phases of operation, of the aerial vehicle. For example, an aerial vehicle may be configured to capture and store a variety of information or data regarding vibrations or other acoustic energies that are generated or encountered during flight. Such information or data may include, but is not limited to, extrinsic information or data, e.g., information or data not directly relating to the aerial vehicle, such as environmental conditions (e.g., temperatures, pressures, humidities, wind speeds and directions), times of day or days of a week, month or year when an aerial vehicle is operating, measures of cloud coverage, sunshine, or surface conditions or textures (e.g., whether surfaces are wet, dry, covered with sand or snow or have any other texture) within a given environment. Such information or data may also include intrinsic information or data, e.g., information or data relating to the aerial vehicle itself, such as operational characteristics (e.g., dynamic attributes such as altitudes, courses, speeds, rates of climb or descent, turn rates, or accelerations; or physical attributes such as dimensions of structures or frames, numbers of propellers or motors, operating speeds of such motors) or tracked positions (e.g., latitudes and/or longitudes) of the aerial vehicles when the acoustic energies are generated or encountered.

In some embodiments, a signature representative of behavior of an aerial vehicle or components thereof may be determined according to modal analysis techniques. Modal analysis is commonly known as a process for determining inherent dynamic characteristics of a system in terms of natural frequencies, damping factors and mode shapes, and using such characteristics to formulate a mathematical model of the system's dynamic behavior. According to a modal analysis theorem, any motion or dynamic response of a system having one or more degrees of freedom may be represented in one or more vectors including products of mass and acceleration, damping and velocity, and stiffness and displacement of each of the discrete parts. For example, a system may be subjected to a vibrational excitation, e.g., from intrinsic or extrinsic sources, and data regarding the system's response to the vibrational excitation may be captured using one or more sensors. A modal analysis may be performed on the data, and one output of the modal analysis may be a spectral density representative of accelerations or vibrations observed in the system in response to the vibrational excitation, based on the captured data.

A mathematical model formulated in response to a modal analysis is sometimes called the "modal model," and the information or data representative of the characteristics by which the modal model is formed is sometimes called the "modal data." In some modal models, a second-order differential equation may represent an excitation force as a sum of a product of a mass matrix and an acceleration, a product of a damping matrix and a velocity, and a product of a stiffness matrix and displacement. Modal analyses may be used to represent any type of vibration or other dynamic activity, e.g., using data obtained from operations or testing, to obtain a definitive description of a response of a structure to forces, thereby resolving the vibration or dynamic activity into a set of simple mode shapes with individual frequency and damping parameters. This description may be represented qualitatively or quantitatively, e.g., as a signature associated with a structure, which can be evaluated against design specifications or other criteria. The description of the response may also be used to construct the modal model, which may itself be used to evaluate effects of operations on the structure, or to predict how the structure will perform and/or respond to changed operating conditions.

When an aerial vehicle returns from a mission, extrinsic information or data and/or intrinsic information or data captured by aerial vehicles during flight may be used in connection with information or data captured during testing of one or more powered elements of the aerial vehicle on the ground, e.g., data captured by not only the onboard sensors but also one or more additional sensors provided in or around a landing area or range. Some or all of the information or data captured by such sensors may be subjected to a modal analysis representative of responses of the aerial vehicle to vibrations and/or other phenomena observed or encountered during operation of the aerial vehicle, or to vibrations and/or other phenomena during the testing of the one or more powered elements on the ground. As a result of the modal analysis, a signature may be determined. The signature, and a prior signature associated with the aerial vehicle (e.g., a baseline signature, or a signature determined following a previous testing evolution), may be provided to one or more machine learning algorithms or functions in order to determine whether the aerial vehicle is operating in a satisfactory or consistent manner, or whether the aerial vehicle is experiencing any faults or discrepancies, or otherwise requires maintenance, repairs or further inspections. For example, using one or more machine learning systems or tools, the information or data captured by the onboard sensors and/or the ground-based sensors may be interpreted in order to determine whether such information or data is representative or indicative of one or more pending or emerging structural deficiencies, such as microfractures, cracks, loosened or broken fasteners, corrosions, fatigue, or evidence of other physical manifestations of stress or strain in one or more components of an aerial vehicle. Moreover, the machine learning systems or tools of the present disclosure may operate in a number of phases or modes.

First, in a training phase or mode, a machine learning system, or one or more computing devices or machines on which the system resides or operates, may receive initial or baseline data regarding an aerial vehicle, e.g., data captured using one or more onboard sensors or ground-based sensors. Such initial or baseline data may include any data regarding operations of the aerial vehicle, or noises or vibrations radiating from an aerial vehicle during such operations, e.g., in one or more pre-commissioning tests or evaluations. In some embodiments, the initial or baseline data provided to the machine learning system may include results of a modal analysis performed on data captured using the one or more onboard sensors or ground-based sensors. For example, where a testing sequence is defined for an aerial vehicle (e.g., a testing sequence associated with each of a plurality of aerial vehicles in a class, or a customized aerial vehicle), in which each of the powered elements or components of the aerial vehicle is operated individually or in tandem, the testing sequence may be performed for an initial or trial run, and acoustic data and imaging data regarding sounds, vibrations or other relevant factors observed during the initial or trial run may be captured from the aerial vehicle. The acoustic data and/or the imaging data captured during the initial or trial run, or a signature determined for the aerial vehicle based on such acoustic data and/or the imaging data, may be provided to the machine learning system as training inputs, and an identifier of a satisfactory or baseline condition of the aerial vehicle may be provided to the machine learning system as a training output. Alternatively, data that is known to be associated with an unsatisfactory condition of the aerial vehicle, or a signature determined based on such data, may be provided to the machine learning system as training inputs, and an identifier of an unsatisfactory or faulted condition of the aerial vehicle may be provided to the machine learning system as a training output.

Next, after the signature has been trained to associate operational or testing data captured from or by an aerial vehicle (e.g., by one or more sensors provided on the aerial vehicle or at a testing facility) with a condition of the aerial vehicle, the machine learning system or tool may receive data regarding operations or testing of the aerial vehicle including but not limited to information or data regarding noises or vibrations radiated from the aerial vehicle during one or more missions, and also noises or vibrations radiated from the aerial vehicle during a testing sequence after the one or more missions have been completed. For example, the machine learning system or tool may receive operational data regarding the aerial vehicle such as courses, speeds, payloads carried, operating runtimes and the like during a mission, and also noises or other vibrations radiated therefrom during the mission, that is captured by one or more onboard sensors, as well as testing data regarding the aerial vehicle captured by the one or more onboard sensors and one or more ground-based sensors after the mission is complete. The operational data and the testing data may be provided to the machine learning system or tool to determine whether the data, individually or collectively, suggests that one or more pending or emerging microfractures, cracks or other structural deficiencies is present, or whether any type or form of maintenance, repairs or further inspections are required.

Those of ordinary skill in the pertinent arts will recognize that any type or form of machine learning system (e.g., hardware and/or software components or modules) may be utilized in accordance with the present disclosure. For example, information or data captured during testing or operation using onboard sensors or ground-based sensors, or a signature or other information determined following a modal analysis of such information or data, may be processed and interpreted according to one or more machine learning algorithms or techniques including but not limited to nearest neighbor methods or analyses, artificial neural networks, conditional random fields, factorization methods or techniques, K-means clustering analyses or techniques, similarity measures such as log likelihood similarities or cosine similarities, latent Dirichlet allocations or other topic models, or latent semantic analyses. Using any of the foregoing algorithms or techniques, or any other algorithms or techniques, information or data regarding the safety or integrity of one or more aerial vehicles, or maintenance, repairs or further inspections required by such vehicles, may be determined.

For example, all data (e.g., acoustic data, imaging data, magnetic data, acceleration data, orientation data, or any other relevant data regarding vibrations experienced during testing or operation, or structural integrity), or signatures representative or determined based on such data, that falls within a predefined threshold or proximity may be placed in or associated with a common cluster or group for a given intensity or frequency of emitted sound or vibration level, or a given level or spectrum of observed accelerations. Such clusters or groups may be defined for an entire set of such data, or, alternatively, among a subset, or a training set, of such data, and extrapolated among the remaining data. Similarly, clusters or groups of characteristics may be defined and associated with aerial vehicles or structural conditions based on co-occurrence frequencies, correlation measurements or any other associations of the characteristics with such vehicles or conditions.

Those of ordinary skill in the pertinent arts will recognize that any type or form of aerial vehicle may be evaluated by one or more of the systems disclosed herein, or in accordance with one or more of the methods disclosed herein, including but not limited to fixed-wing or rotating-wing aircraft. Moreover, such evaluations may be conducted while the aerial vehicle is performed or being subjected to one or more other tasks. For example, data may be captured from an aerial vehicle performing a predetermined testing sequence, e.g., operating each of the motors and rotors and/or control surfaces of the aerial vehicle independently or in tandem, while the aerial vehicle is being loaded with a new payload or otherwise being prepared to perform a new mission. If the data indicates that no maintenance, repairs or further inspections are required, the aerial vehicle may be cleared to perform the new mission at the earliest opportunity. If the data indicates that maintenance, repairs or further inspections may be needed, however, the aerial vehicle may be blocked from the new mission until any faults have been identified and addressed. Additionally, such evaluations may also be conducted while an aerial vehicle is traveling, e.g., across a range or over or near a predetermined point, or performing any other functions. Moreover, data captured during operations or testing may be subjected to processing (e.g., one or more modal analyses of such data) in real time, in near-real time, or in one or more batch processes in accordance with the present disclosure.

Figure 2:
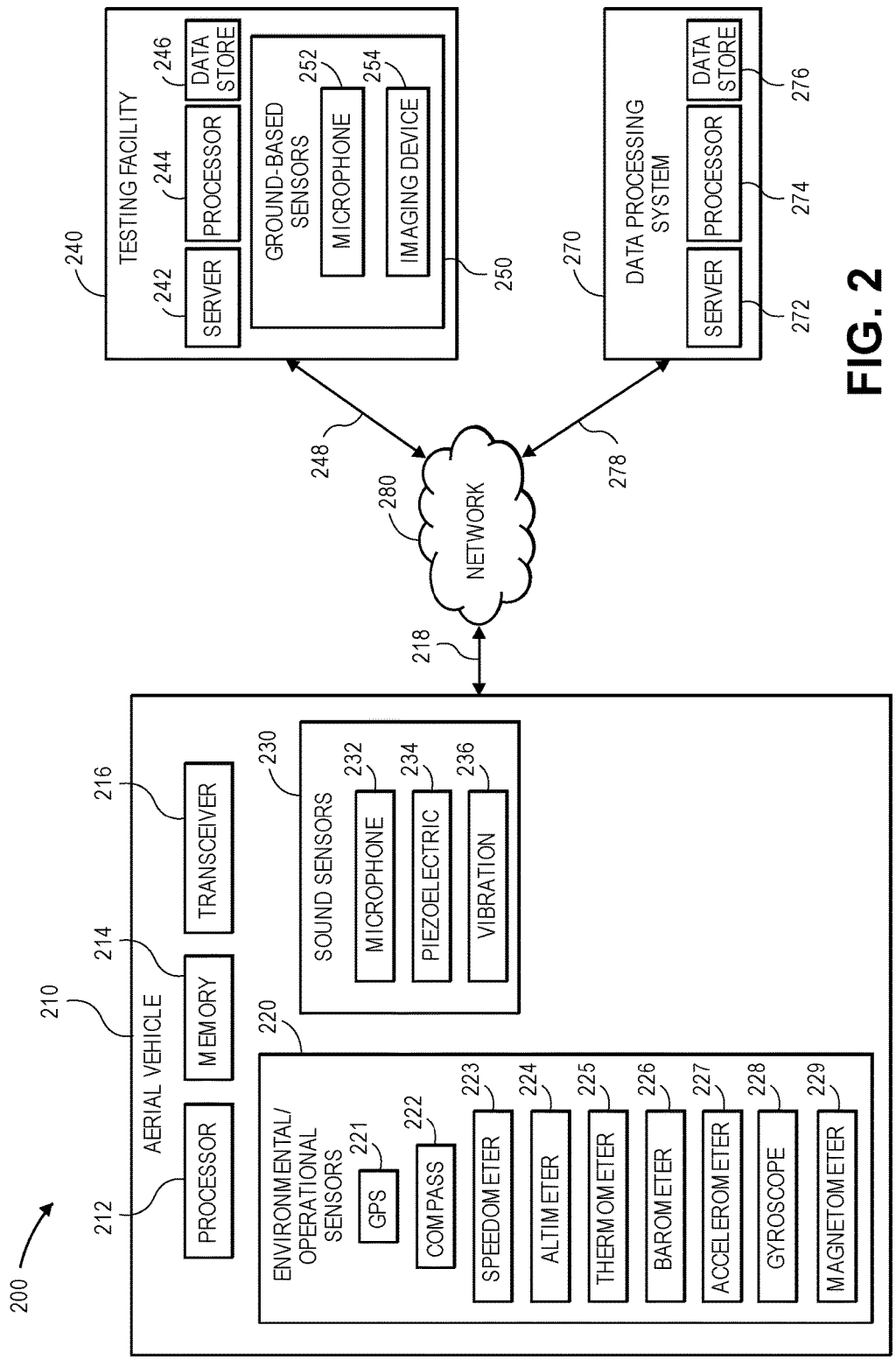
FIG. 2 is a block diagram of one system for automated aerial vehicle inspections in accordance with embodiments of the present disclosure.

Referring to FIG. 2, a block diagram of components of one system 200 for automated aerial vehicle inspections in accordance with embodiments of the present disclosure is shown. The system 200 of FIG. 2 includes an aerial vehicle 210, a testing facility 240 and a data processing system 270 connected to one another over a network 280. Except where otherwise noted, reference numerals preceded by the number "2" shown in the block diagram of FIG. 2 indicate components or features that are similar to components or features having reference numerals preceded by the number "1" shown in FIGS. 1A through 1D.

The aerial vehicle 210 includes a processor 212, a memory 214 and a transceiver 216, as well as a plurality of environmental or operational sensors 220 and a plurality of sound sensors 230.

The processor 212 may be configured to perform any type or form of computing function, including but not limited to the execution of one or more analytical functions or machine learning algorithms or techniques. For example, the processor 212 may control any aspects of the operation of the aerial vehicle 210 and the one or more computer-based components thereon, including but not limited to the transceiver 216, the environmental or operational sensors 220, and/or the sound sensors 230. The aerial vehicle 210 may likewise include one or more control systems (not shown) that may generate instructions for conducting operations thereof, e.g., for operating one or more rotors, motors, rudders, ailerons, flaps or other components provided thereon. Such control systems may be associated with one or more other computing devices or machines, and may communicate with the testing facility 240 and/or the data processing system 270 or one or more other computer devices (not shown) over the network 280, through the sending and receiving of digital data. The aerial vehicle 210 further includes one or more memory or storage components 214 for storing any type of information or data, e.g., instructions for operating the aerial vehicle, or information or data captured by one or more of the environmental or operational sensors 220 and/or the sound sensors 230.

The transceiver 216 may be configured to enable the aerial vehicle 210 to communicate through one or more wired or wireless means, e.g., wired technologies such as Universal Serial Bus (or "USB") or fiber optic cable, or standard wireless protocols such as Bluetooth® or any Wireless Fidelity (or "WiFi") protocol, such as over the network 280 or directly.

The environmental or operational sensors 220 may include any components or features for determining one or more attributes of an environment in which the aerial vehicle 210 is operating, or may be expected to operate, including extrinsic information or data or intrinsic information or data. As is shown in FIG. 2, the environmental or operational sensors 220 may include, but are not limited to, a Global Positioning System ("GPS") receiver or sensor 221, a compass 222, a speedometer 223, an altimeter 224, a thermometer 225, a barometer 226, an accelerometer 227, or a gyroscope 228. The GPS sensor 221 may be any device, component, system or instrument adapted to receive signals (e.g., trilateration data or information) relating to a position of the handheld device 250 from one or more GPS satellites of a GPS network (not shown). The compass 222 may be any device, component, system, or instrument adapted to determine one or more directions with respect to a frame of reference that is fixed with respect to the surface of the Earth (e.g., a pole thereof). The speedometer 223 may be any device, component, system, or instrument for determining a speed or velocity of the aerial vehicle 210, and may include related components (not shown) such as pitot tubes, accelerometers, or other features for determining speeds, velocities, or accelerations.

The altimeter 224 may be any device, component, system, or instrument for determining an altitude of the aerial vehicle 210, and may include any number of barometers, transmitters, receivers, range finders (e.g., laser or radar) or other features for determining heights. The thermometer 225 and the barometer 226 may be any devices, components, systems, or instruments for determining local air temperatures or atmospheric pressures, respectively, within a vicinity of the aerial vehicle 210. The accelerometer 227 may be any mechanical or electrical device, component, system, or instrument for sensing or measuring accelerations, including but not limited to devices having one or more potentiometers, linear variable differential transformers, variable reluctance devices or piezoelectric components.

The gyroscope 228 may be any mechanical or electrical device, component, system, or instrument for determining an orientation, e.g., the orientation of the aerial vehicle 210. For example, the gyroscope 228 may be a traditional mechanical gyroscope having at least a pair of gimbals and a flywheel or rotor. Alternatively, the gyroscope 228 may be an electrical component such a dynamically tuned gyroscope, a fiber optic gyroscope, a hemispherical resonator gyroscope, a London moment gyroscope, a microelectromechanical sensor gyroscope, a ring laser gyroscope, or a vibrating structure gyroscope, or any other type or form of electrical component for determining an orientation of the aerial vehicle 210. The magnetometer 229 may be any electrical component for measuring a strength of a magnetic field, such as a vector magnetometer or a scalar magnetometer (e.g., a proton precession magnetometer, an Overhauser magnetometer, an ionized gas magnetometer, a rotating coil magnetometer, a Hall Effect magnetometer, or the like).

Those of ordinary skill in the pertinent arts will recognize that the environmental or operational sensors 220 may include any type or form of device or component for determining an environmental condition within a vicinity of the aerial vehicle 210 in accordance with the present disclosure. For example, the environmental or operational sensors 220 may include one or more air monitoring sensors (e.g., oxygen, ozone, hydrogen, carbon monoxide or carbon dioxide sensors or hygrometers), infrared sensors, ozone monitors, pH sensors, magnetic anomaly detectors, metal detectors, radiation sensors (e.g., Geiger counters, neutron detectors, alpha detectors), attitude indicators, depth gauges or the like, as well as one or more imaging devices (e.g., digital cameras), and are not limited to the sensors 221, 222, 223, 224, 225, 226, 227, 228, 229 shown in FIG. 2.

The sound sensors 230 may include other components or features for detecting and capturing sound energy in a vicinity of an environment in which the aerial vehicle 210 is operating, or may be expected to operate. As is shown in FIG. 2, the sound sensors 230 may include a microphone 232, a piezoelectric sensor 234, and a vibration sensor 236. The microphone 232 may be any type or form of transducer (e.g., a dynamic microphone, a condenser microphone, a ribbon microphone, a crystal microphone) configured to convert acoustic energy of any intensity and across any or all frequencies into one or more electrical signals, and may include any number of diaphragms, magnets, coils, plates, or other like features for detecting and recording such energy. The microphone 232 may also be provided as a discrete component, or in combination with one or more other components, e.g., an imaging device such as a digital camera. Furthermore, the microphone 232 may be configured to detect and record acoustic energy from any and all directions.

The piezoelectric sensor 234 may be configured to convert changes in pressure to electrical signals, including but not limited to such pressure changes that are initiated by the presence of acoustic energy across various bands of frequencies, and may include one or more crystals, electrodes or other features. The vibration sensor 236 may be any device configured to detect vibrations of one or more components of the aerial vehicle 210, and may also be a piezoelectric device. For example, the vibration sensor 236 may include one or more accelerometers, e.g., an application-specific integrated circuit and one or more microelectromechanical sensors in a land grid array package, that are configured to sense differential accelerations along one or more axes over predetermined periods of time and to associate such accelerations with levels of vibration and, therefore, sound.

The testing facility 240 may be any facility, structure, station or other location where one or more automated inspections may be performed on one or more aerial vehicles, such as the aerial vehicle 210. The testing facility 240 may include one or more features or components for enabling arrivals or departures of aerial vehicles therefrom, such as the landing pad 145 shown in FIGS. 1A through 1D. In some embodiments, the testing facility 240 may be provided in association with one or more facilities, structures, stations or locations associated with one or more missions to be performed by the aerial vehicle 210, e.g., delivery or surveillance operations. In some other embodiments, the testing facility 240 may be an independent or freestanding facility, structure, station or location not associated with any one specific mission.

As is shown in FIG. 2, the testing facility 240 includes a number of computer components, including one or more physical computer servers 242 having a plurality of databases 244 associated therewith, as well as one or more computer processors 246. The testing facility 240 further includes a plurality of sensors 250, including but not limited to one or more microphones 252 (or other acoustic sensors) and one or more imaging devices 254 (e.g., digital cameras).

The servers 242, the databases 244 and the processors 246 may be provided for controlling any aspect of the operations of the testing facility 240, including but not limited to receiving, analyzing and/or storing information or data captured by the environmental or operational sensors 220, the sound sensors 230 and/or the facility sensors 250. For example, in accordance with some embodiments of the present disclosure, the servers 242 and/or the processors 246 may transmit instructions to one or more aerial vehicles, e.g., the aerial vehicle 210, regarding a testing sequence to be performed thereby at the testing facility 240. The servers 242 and/or the processors 246 may also receive information or data from the one or more aerial vehicles regarding operational data captured during the performance of one or more missions, e.g., by the environmental or operational sensors 220 or the sound sensors 230, and/or testing data captured during the execution of a testing sequence, e.g., by either the environmental or operational sensors 220, the sound sensors 230 or the facility sensors 250, and store such information or data in the one or more databases 244. Additionally, the servers 242 and/or the processors 246 may also communicate with one or more other computer devices (not shown) over the network 280, as indicated by line 248, through the sending and receiving of digital data.

Like the microphone 232, the microphone 252 may be any type or form of transducer (e.g., a dynamic microphone, a condenser microphone, a ribbon microphone, a crystal microphone) configured to convert acoustic energy of any intensity and across any or all frequencies into one or more electrical signals, and may include any number of diaphragms, magnets, coils, plates, or other like features for detecting and recording such energy. The microphone 252 may also be provided as a discrete component, or in combination with one or more other components, e.g., an imaging device such as a digital camera. Furthermore, the microphone 252 may be configured to detect and record acoustic energy from any and all directions. In addition to microphones, the testing facility 250 may utilize or operate any number of other acoustic sensors, e.g., piezoelectric sensors 234 and/or vibration sensors 236.

The imaging device 254 may be any form of optical recording device that may be used to photograph or otherwise record imaging data of aerial vehicles within the testing facility 240, or for any other purpose. The imaging device 254 may include one or more sensors, memory or storage components and processors, and such sensors, memory components or processors may further include one or more photosensitive surfaces, filters, chips, electrodes, clocks, boards, timers or any other relevant features (not shown). Such imaging devices 254 may capture imaging data in the form of one or more still or moving images of any kind or form, as well as any relevant audio signals or other information, within one or more designated locations within the testing facility 240, and may be connected to the server 242 and/or the processor 244 or with one another by way of a wired or wireless connection that may be dedicated or comprise all or part of an internal network (not shown). Additionally, the imaging device 254 may be adapted or otherwise configured to communicate with the aerial vehicle 210 or the data processing system 270, or to access one or more other computer devices by way of the network 280.

Moreover, the imaging device 254 may also include manual or automatic features for modifying a respective position, field of view or orientation. For example, a digital camera may be configured in a fixed position, or with a fixed focal length (e.g., fixed-focus lenses) or angular orientation. Alternatively, the imaging device 254 may include one or more actuated or motorized features for adjusting a position of the imaging device 254, or for adjusting either the focal length (e.g., zooming the imaging device 254) or the angular orientation (e.g., the roll angle, the pitch angle or the yaw angle), by causing a change in the distance between the sensor and the lens (e.g., optical zoom lenses or digital zoom lenses), a change in the location of the imaging device 254, or a change in one or more of the angles defining the angular orientation.

For example, the imaging device 254 may be hard-mounted to a support or mounting that maintains the device in a fixed configuration or angle with respect to one, two or three axes. Alternatively, however, the imaging device 254 may be provided with one or more motors and/or controllers for manually or automatically operating one or more of the components, or for reorienting a position, axis or direction of the imaging device 254, i.e., by moving, panning or tilting the imaging device 254. Panning the imaging device 254 may cause a rotation within a horizontal plane or about a vertical axis (e.g., a yaw), while tilting the imaging device 254 may cause a rotation within a vertical plane or about a horizontal axis (e.g., a pitch). Additionally, the imaging device 254 may be rolled, or rotated about its axis of rotation, and within a plane that is perpendicular to the axis of rotation and substantially parallel to a field of view of the imaging device 254. The imaging device 254 may also be provided on a vehicle enabled to pass within an operating range of the aerial vehicle 210.

The imaging device 254 may also digitally or electronically adjust an image identified in a field of view, subject to one or more physical and operational constraints. For example, the imaging device 254 may virtually stretch or condense the pixels of an image in order to focus or broaden the field of view of the imaging device 254, and also translate one or more portions of images within the field of view. Imaging devices having optically adjustable focal lengths or axes of orientation are commonly referred to as pan-tilt-zoom (or "PTZ") imaging devices, while imaging devices having digitally or electronically adjustable zooming or translating features are commonly referred to as electronic PTZ (or "ePTZ") imaging devices.

Although the testing facility 240 of FIG. 2 includes a single box corresponding to one microphone 252 and a single box corresponding to one imaging device 254, those of ordinary skill in the pertinent arts will recognize that any number or type of microphones or imaging devices may be provided at the testing facility 240 in accordance with the present disclosure. Moreover, in addition to the microphone 252 and the imaging device 254, the testing facility 240 may be configured or equipped with one or more other ground-based sensors, including but not limited to accelerometers, gyroscopes and/or magnetometers, or other sound sensors or imaging devices.

The data processing system 270 includes one or more physical computer servers 272 having a plurality of databases 274 associated therewith, as well as one or more computer processors 276 provided for any specific or general purpose. For example, the data processing system 270 of FIG. 2 may be independently provided for the exclusive purpose of receiving, analyzing or storing acoustic signals or other information or data received from the aerial vehicle 210 or, alternatively, provided in connection with one or more physical or virtual services configured to receive, analyze or store such acoustic signals, information or data, as well as one or more other functions. The servers 272 may be connected to or otherwise communicate with the databases 274 and the processors 276. The databases 274 may store any type of information or data, including but not limited to acoustic signals, information or data relating to acoustic signals, or information or data regarding environmental conditions, operational characteristics, or positions, for any purpose. The servers 272 and/or the computer processors 276 may also connect to or otherwise communicate with the network 280, as indicated by line 278, through the sending and receiving of digital data. For example, the data processing system 270 may include any facilities, stations or locations having the ability or capacity to receive and store information or data, such as media files, in one or more data stores, e.g., media files received from the aerial vehicle 210, or from one another, or from one or more other external computer systems (not shown) via the network 280. In some embodiments, the data processing system 270 may be provided in a physical location. In other such embodiments, the data processing system 270 may be provided in one or more alternate or virtual locations, e.g., in a "cloud"-based environment. In still other embodiments, the data processing system 270 may be provided onboard one or more aerial vehicles, including but not limited to the aerial vehicle 210.

The network 280 may be any wired network, wireless network, or combination thereof, and may comprise the Internet in whole or in part. In addition, the network 280 may be a personal area network, local area network, wide area network, cable network, satellite network, cellular telephone network, or combination thereof. The network 280 may also be a publicly accessible network of linked networks, possibly operated by various distinct parties, such as the Internet. In some embodiments, the network 280 may be a private or semi-private network, such as a corporate or university intranet. The network 280 may include one or more wireless networks, such as a Global System for Mobile Communications (GSM) network, a Code Division Multiple Access (CDMA) network, a Long Term Evolution (LTE) network, or some other type of wireless network. Protocols and components for communicating via the Internet or any of the other aforementioned types of communication networks are well known to those skilled in the art of computer communications and thus, need not be described in more detail herein.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, link, node, hub or any other aspect of the present disclosure.

The aerial vehicle 210, the testing facility 240 or the data processing system 270 may use any web-enabled or Internet applications or features, or any other client-server applications or features including E-mail or other messaging techniques, to connect to the network 280, or to communicate with one another, such as through short or multimedia messaging service (SMS or MMS) text messages. For example, the aerial vehicle 210 may be adapted to transmit information or data in the form of synchronous or asynchronous messages to the testing facility 240 or the data processing system 270 or to any other computer device in real time or in near-real time, or in one or more offline processes, via the network 280. Those of ordinary skill in the pertinent art would recognize that the aerial vehicle 210, the testing facility 240 or the data processing system 270 may operate, include or be associated with any of a number of computing devices that are capable of communicating over the network, including but not limited to set-top boxes, personal digital assistants, digital media players, web pads, laptop computers, desktop computers, electronic book readers, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the processor 212, the processor 244 or the processor 274, or any other computers or control systems utilized by the aerial vehicle 210, the testing facility 240 or the data processing system 270, and having sequences of instructions which, when executed by a processor (e.g., a central processing unit, or "CPU"), cause the processor to perform all or a portion of the functions, services and/or methods described herein. Such computer executable instructions, programs, software, and the like may be loaded into the memory of one or more computers using a drive mechanism associated with the computer readable medium, such as a floppy drive, CD-ROM drive, DVD-ROM drive, network interface, or the like, or via external connections.

Some embodiments of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, embodiments may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Figure 3:
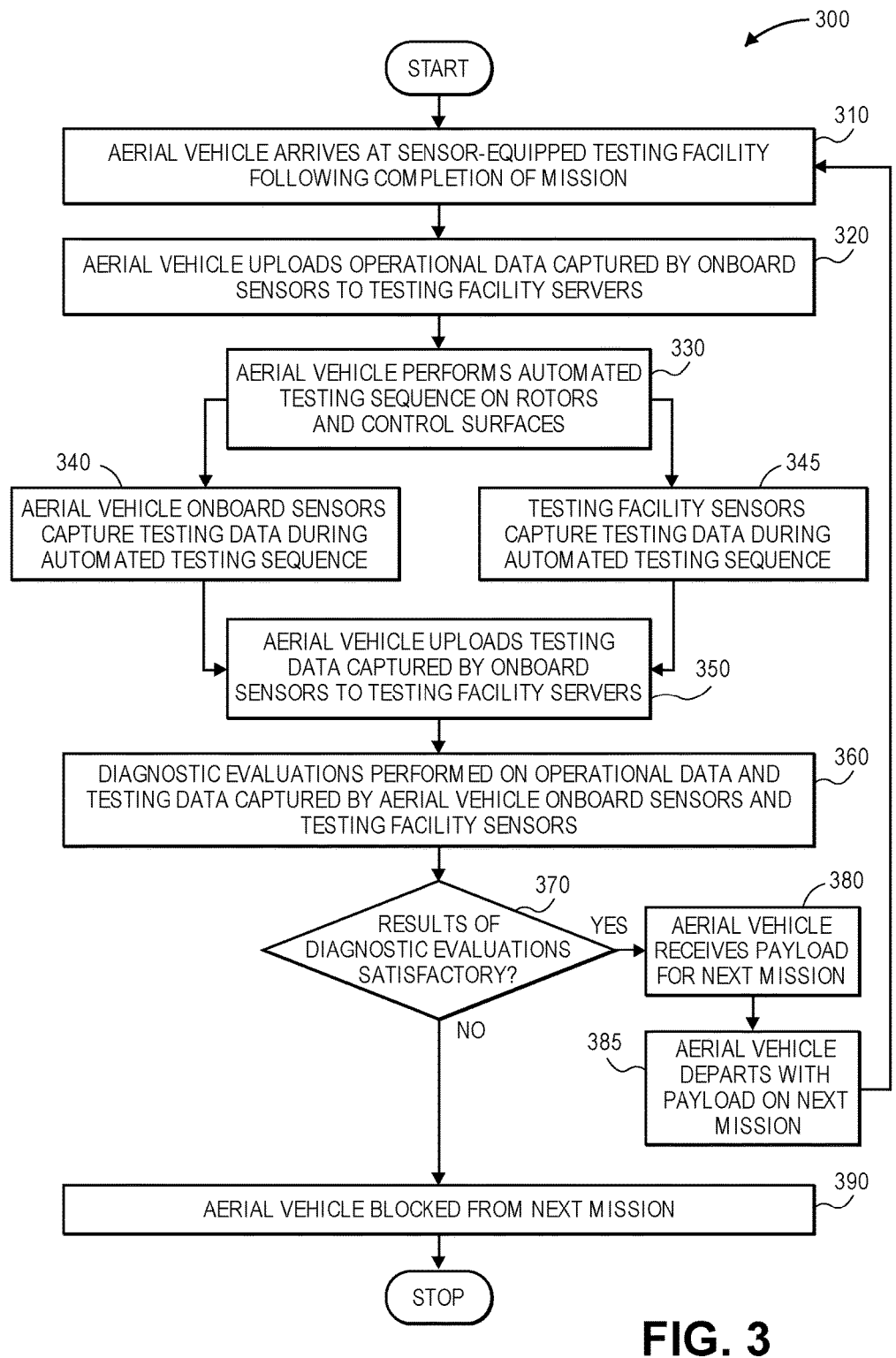
FIG. 3 is a flow chart of one process for automated aerial vehicle inspections in accordance with embodiments of the present disclosure.

As is discussed above, an aerial vehicle may be evaluated following a completed mission based on information or data captured both by one or more onboard sensors during the mission and also by the onboard sensors and one or more ground-based sensors after the mission has been completed, or between two phases of operation of the aerial vehicle. Referring to FIG. 3, a flow chart 300 of one process for automated aerial vehicle inspections in accordance with embodiments is shown. At box 310, an aerial vehicle arrives at a sensor-equipped testing facility following the completion of a mission. For example, the aerial vehicle may have been tasked with delivering a payload from one location to another location, performing one or more law enforcement or surveillance operations, or any other mission. The testing facility may be located at an origin of the mission, a destination for the mission, or an intermediate or other point that is neither the origin nor the destination.

At box 320, the aerial vehicle uploads operational data that was captured by onboard sensors during the mission to testing facility servers. For example, such information may include extrinsic information or data, e.g., environmental conditions encountered during the mission, as well as intrinsic information or data, e.g., dynamic attributes such as altitudes, courses, speeds, rates of climb or descent, turn rates, or accelerations of the aerial vehicle during the mission, or noise or vibrations radiated thereby, and may be transferred to one or more servers via wired or wireless means.

At box 330, the aerial vehicle performs an automated testing sequence on the rotors and control surfaces. For example, the aerial vehicle may operate each of the motors and/or rotors provided thereon independently or in tandem, at any range of operating speeds, and may cause control surfaces such as rudders, elevators, stabilizers, spoilers, ailerons, flaps or slats to move within any range of operation (e.g., linear or angular displacement). At box 340, the aerial vehicle's onboard sensors capture testing data during the performance of the automated testing sequence, while in parallel, at box 345, the testing facility's sensors capture testing data during the performance of the automated testing sequence. For example, referring again to FIGS. 1C and 1D, the aerial vehicle 110 may operate each of the motors 113-1, 113-2, 113-3, 113-4 within acoustic ranges of the microphones 152-1, 152-2 and within fields of view of the imaging devices 154-1, 154-2, and also within operational ranges of any other sensors (not shown) provided at the testing facility 140. At box 350, the aerial vehicle uploads the testing data that it captured to the testing facility servers.

At box 360, one or more diagnostic evaluations are performed on the operational data and the testing data captured by the aerial vehicle onboard sensors and the ground-based testing facility sensors. The diagnostic evaluations may be used to determine whether the aerial vehicle is operating properly or effectively, or whether the aerial vehicle is experiencing one or more microfractures, cracks, loosened or broken fasteners, corrosions, fatigue, or evidence of other physical manifestations of stress or strain. The aerial vehicle may operate differently, both visibly and audibly, or in other manners, when the aerial vehicle requires maintenance, repairs or further inspections as compared to when the aerial vehicle is newly constructed or has just completed maintenance, repairs or further inspections. For example, in some embodiments, a signature may be defined for the operation of the aerial vehicle based on the operational data, the testing data or a combination of the operational data and the testing data, which may include imaging data captured at high frame rates, acoustic data captured using one or more microphones or other acoustic devices, magnetic data captured using one or more magnetometers, or any other sensed data. The signature may be compared to a baseline signature for the aerial vehicle, a predicted signature for the aerial vehicle based on the aerial vehicle's age, run time or operating history or characteristics, or any other standard.

At box 370, if the results of the diagnostic evaluations are satisfactory, then the process advances to box 380, where the aerial vehicle receives a payload for its next mission, and to box 385, where the aerial vehicle departs with the payload on its next mission. If the results of the diagnostic evaluations are unsatisfactory, however, then the process advances to box 390, where the aerial vehicle is blocked from its next mission, and the process ends. For example, the aerial vehicle may be taken out-of-service based for a manual or visual inspection to determine the cause for any deviations or non-compliant aspects of the diagnostic evaluations, or to implement one or more repairs to the aerial vehicle. In some embodiments, the cause of the unsatisfactory diagnostic evaluations may be readily apparent from the operational data and/or testing data itself, and a manual or visual inspection need not be necessary prior to initiating repairs.

Figure 4A:
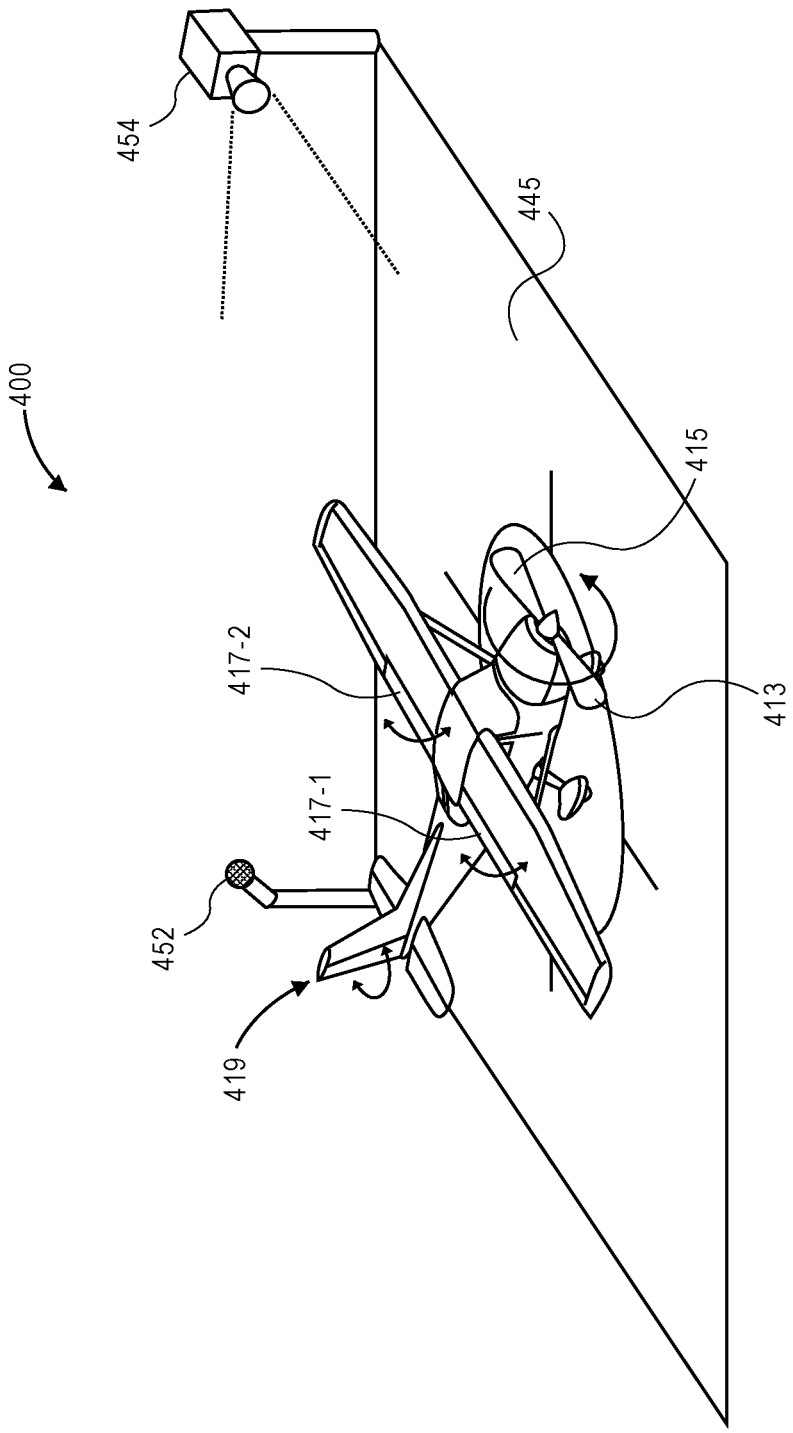
FIGS. 4A through 4C are views of aspects of one system for automated aerial vehicle inspections in accordance with embodiments of the present disclosure.
Figure 4B:
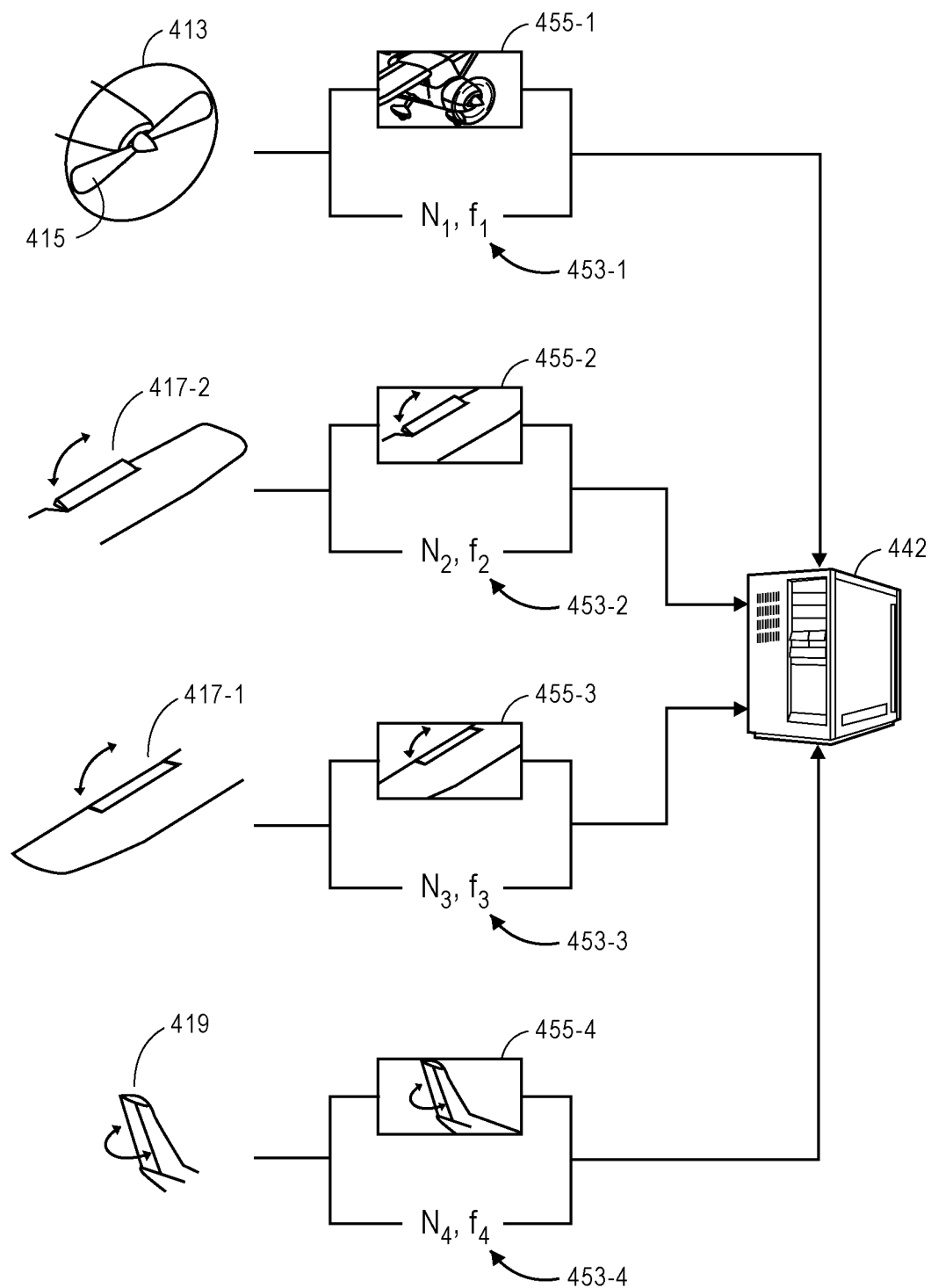
Figure 4C:
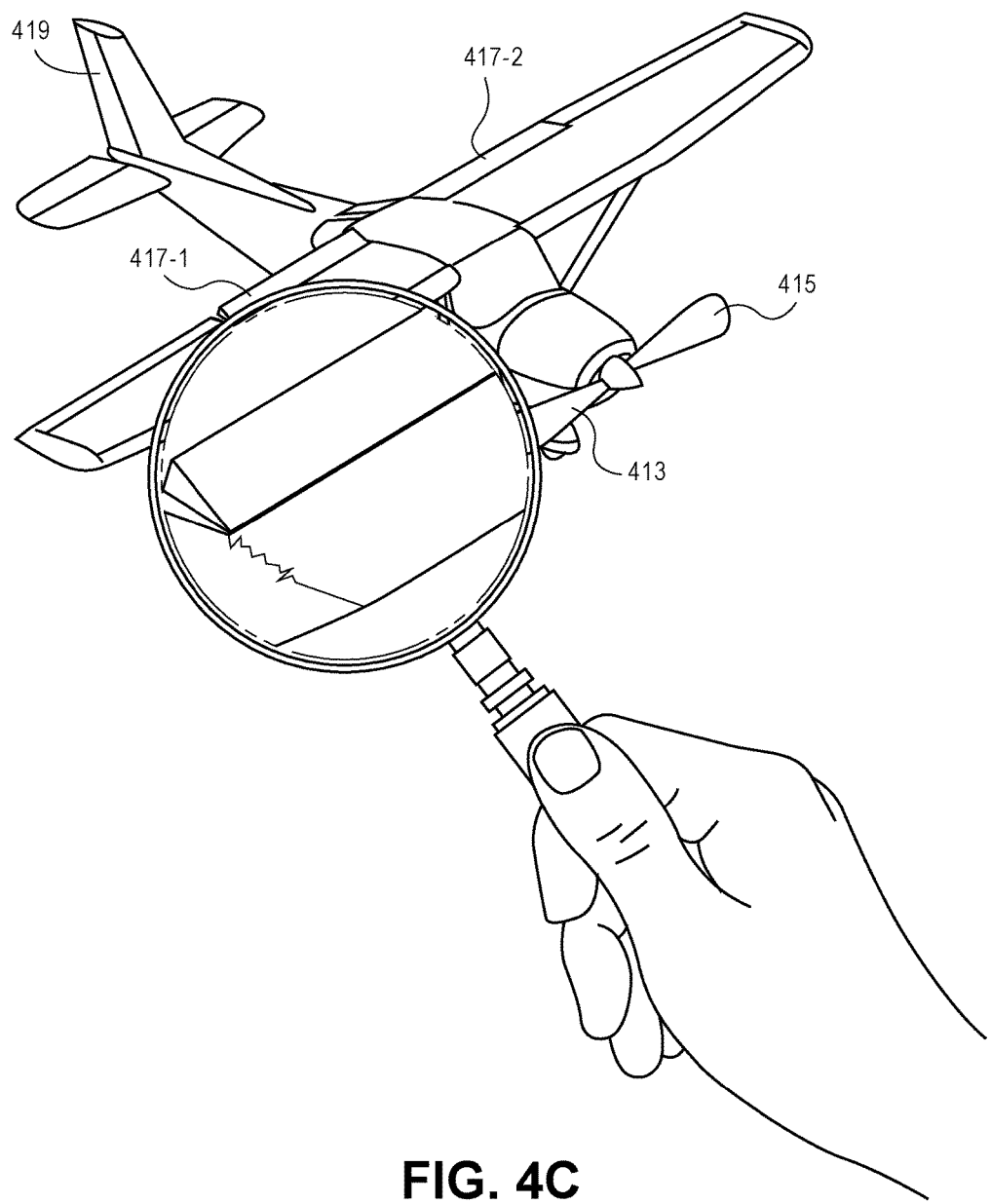

As is discussed above, the automated inspection systems and methods disclosed herein may be performed on any type of aerial vehicle, and based on automated testing sequences that operate each of the rotors, motors, engines, control surfaces or other aspects of the aerial vehicle within a field of view and/or an acoustic range of one or more sensors. Referring to FIGS. 4A through 4C, views of aspects of one system 400 for automated aerial vehicle inspections in accordance with embodiments of the present disclosure are shown. As is shown in FIG. 4A, an aerial vehicle 410 is shown on a landing area 445 at a testing facility 440. Except where otherwise noted, reference numerals preceded by the number "4" shown in FIGS. 4A through 4C indicate components or features that are similar to components or features having reference numerals preceded by the number "2" shown in FIG. 2 or by the number "1" shown in FIGS. 1A through 1D.

The aerial vehicle 410 includes a motor 413, a rotor 415, a pair of ailerons 417-1, 417-2 or flaps and a rudder 419. The testing facility 440 includes a microphone 452 and an imaging device 454 aligned to capture acoustic data or imaging data from aerial vehicles 410 operating within the landing area 445.

The motor 413 is configured to rotate the rotor 415 about an axis defined by a shaft (not shown) of the motor 413. The ailerons 417-1, 417-2 are hinged control surfaces that are aligned along trailing edges of the wings of the aerial vehicle 410 and may be operated in order to cause a change in a lift vector (e.g., a vertical direction of force) of the aerial vehicle 410 during flight, e.g., by rotating the ailerons 417-1, 417-2 about the hinges above or below the wings within a predefined angular range. The rudder 419 is another hinged control surface that is aligned along a trailing edge of a tail of the aerial vehicle 410 and may be operated in order to cause a change in a thrust vector (e.g., a horizontal direction of force) of the aerial vehicle 410 during flight, e.g., by rotating the rudder 419 about the hinge to a left or a right of the tail within a predefined angular range.

In accordance with the present disclosure, upon an arrival of the aerial vehicle 410 at the landing area 445, or at any other time between phases of operation of the aerial vehicle 410, the aerial vehicle 410 may be operated according to a testing sequence, e.g., independently and/or in tandem, within an acoustic range of the microphone 452 and a field of view of the imaging device 454. For example, as is shown in FIG. 4B, the motor 413 may cause the rotor 415 to rotate, and acoustic data 453-1 (e.g., sound pressure levels and/or frequency spectrums) and imaging data 455-1 (e.g., a series of images, preferably captured at high frame rates) may be captured from the aerial vehicle 410 in general, and from the motor 413 and the rotor 415 in particular, as the motor 413 and the rotor 415 are operating at any range of operational speeds. Similarly, as is also shown in FIG. 4B, acoustic data 453-2 and imaging data 455-2 are captured during operation of the aileron 417-2, while acoustic data 453-3 and imaging data 455-3 are captured during the operation of the aileron 417-1, and acoustic data 453-4 and imaging data 455-4 are captured during the operation of the rudder 419. The acoustic data 453-1, 453-2, 453-3, 453-4 and the imaging data 455-1, 455-2, 455-3, 455-4 may, once captured, be transferred to one or more servers 442 associated with the testing facility 440, e.g., in the same physical location, or in one or more alternate or virtual locations, such as in a "cloud"-based environment.

Using the one or more servers 442, the acoustic data 453-1, 453-2, 453-3, 453-4 and the imaging data 455-1, 455-2, 455-3, 455-4 are processed to determine whether any of the data is out-of-specification or otherwise indicates that maintenance, repairs or further inspections may be required. For example, in some embodiments, spectral densities of measured accelerations, including linear accelerations, angular accelerations, or both linear and angular accelerations, may be compared to a baseline or predicted signature, and any deviations between the spectral densities and the baseline or predicted signature may indicate that the aerial vehicle 410 requires maintenance, repairs or further inspections as a whole, or that one or more specific elements of the aerial vehicle 410 require maintenance, repairs or further inspections.

As is shown in FIG. 4C, when the acoustic data 453-3 and the imaging data 455-3 captured during the operation of the aileron 417-1 is determined to be out-of-specification, one or more manual or visual inspections of the aileron 417-1 may be conducted in order to search for microfractures, cracks, loosened or broken fasteners, corrosions, fatigue, or evidence of other physical manifestations of stress or strain. Although the landing area 445 of FIG. 4A includes just a pair of sensors, viz., the microphone 452 and the imaging device 454, those of ordinary skill in the pertinent arts will recognize that testing facilities may include any number of sensors, of any type (e.g., not only imaging devices or acoustic sensors but also magnetometers or any other sensors), and that data captured using such sensors may be used to determine whether an aerial vehicle requires maintenance or inspection.

As is discussed above, determinations as to whether an aerial vehicle is experiencing any faults or discrepancies, or otherwise requires maintenance or repair, may be made based on comparisons of testing data (e.g., acoustic data, imaging data, magnetic data, vibration data, or data regarding radiated noise) captured during an execution of a predetermined testing sequence between phases of operation of the aerial vehicle, and baseline data or predicted data. For example, where data regarding accelerations or vibrations of all or portions of an aerial vehicle is measured during operations or testing, a spectral density of the measured data and/or the accelerations or vibrations may be compared to a baseline signature generated following an initial execution of the predetermined testing sequence prior to initiating operations with the aerial vehicle, or a signature generated following any prior execution of the predetermined testing sequence.

Figure 5A:
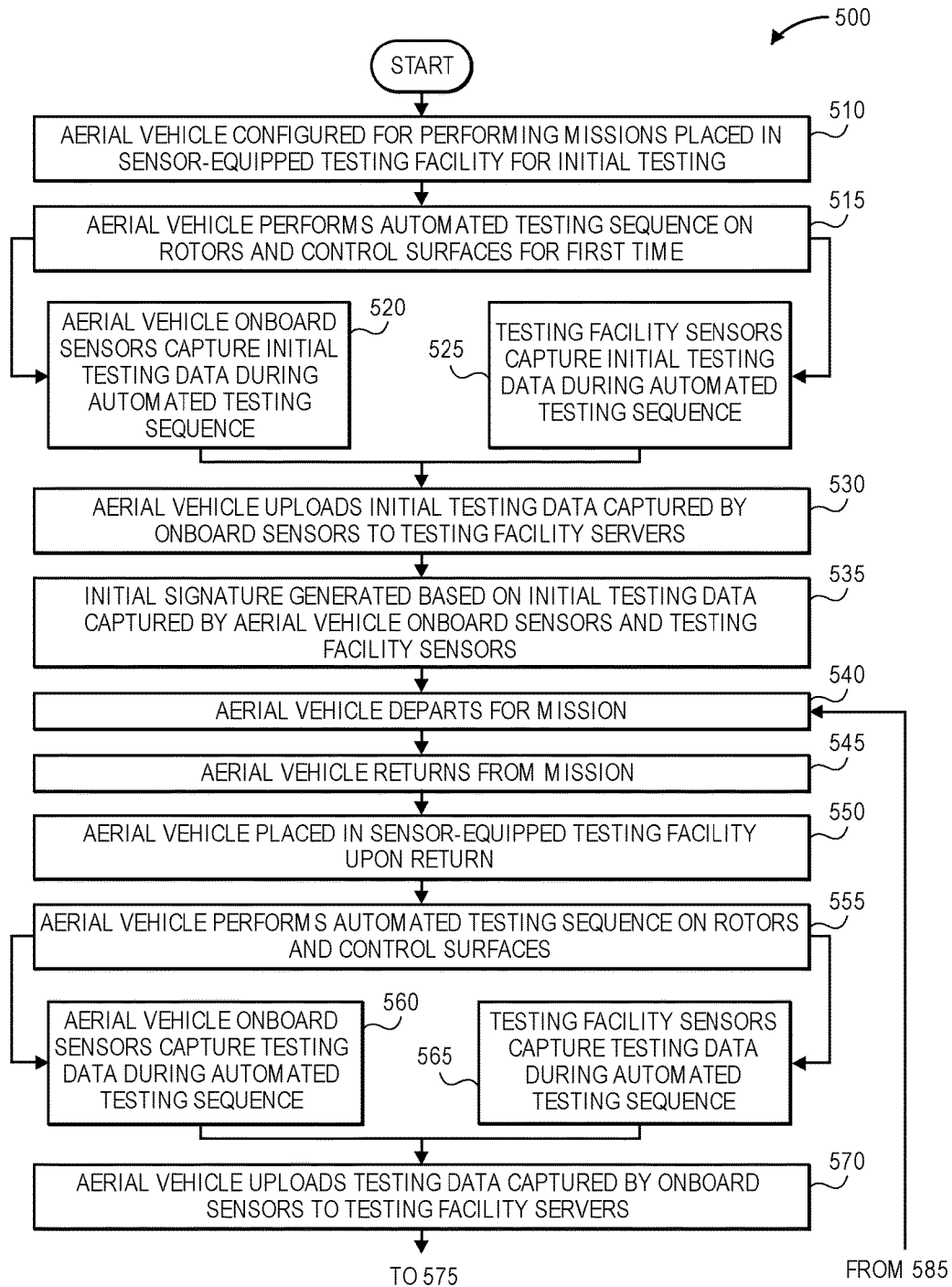
FIGS. 5A and 5B are a flow chart of one process for automated aerial vehicle inspections in accordance with embodiments of the present disclosure.
Figure 5B:
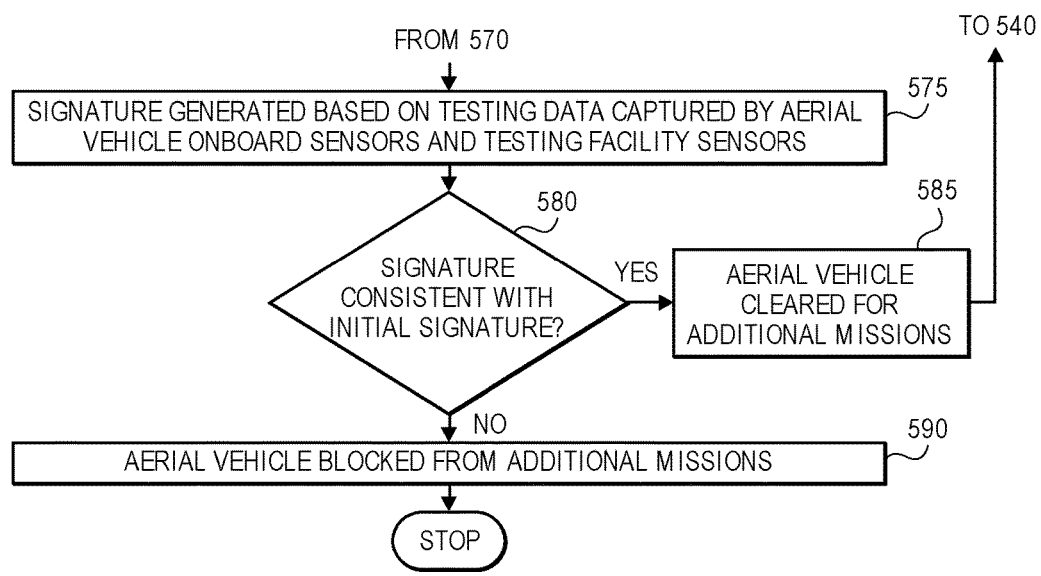

Referring to FIGS. 5A and 5B, a flow chart 500 of one process for automated aerial vehicle inspections in accordance with embodiments of the present disclosure is shown. At box 510, an aerial vehicle configured for performing missions is placed in a sensor-equipped testing facility for initial testing. For example, the aerial vehicle may be transported, carried or delivered to a location at a testing facility, such as the landing pad 145 of FIGS. 1A through 1D or the landing area 445 of FIG. 4A, that is outfitted with one or more sensors, e.g., acoustic sensors, imaging devices, magnetometers or other sensors. At box 515, an automated testing sequence may be performed on the rotors and control surfaces of the aerial vehicle for the first time, e.g., within operating ranges of the sensors at the testing facility. For example, the aerial vehicle may be subjected to a shakedown operation following an initial construction or assembly, or after a maintenance evolution has been completed.

At box 520, sensors onboard the aerial vehicle capture initial testing data during the performance of the automated testing sequence, while in parallel, at box 525, sensors at the testing facility capture initial testing data during the performance of the automated testing sequence. For example, any acoustic sensors, imaging devices, gyroscopes, accelerometers, magnetometers or other sensors provided on the aerial vehicle or at the testing facility may remain operating and capturing data while the various motors, rotors, rudders, elevators, stabilizers, spoilers, ailerons, flaps or slats on the aerial vehicle are operated either individually or in tandem. At box 530, the aerial vehicle uploads the initial testing data captured by the onboard sensors to one or more servers at the testing facility, which may be in communication with the testing facility sensors, as well.

At box 535, an initial signature is generated based on the initial testing data captured by the aerial vehicle onboard sensors and testing facility sensors. For example, the initial signature may be generated based on one or more sound pressure levels or frequency spectrums radiating from one or more components of the aerial vehicle, which may be captured by either the onboard sensors or the ground-based sensors. Likewise, the initial signature may be generated based on vibration levels or data detected by an onboard gyroscope during the operation of the one or more components. Moreover, the initial signature may further take into account observed vibrations or activity represented in imaging data captured by one or more onboard or ground-based imaging devices, e.g., high frame rate digital cameras. Any type of form of testing data captured during an initial performance of the automated testing sequence may be considered and incorporated into an initial signature, which may be generated by any algorithm or function. For example, some or all of the testing data captured by the onboard sensors and/or the ground-based sensors may be provided to a machine learning system or tool operated by servers at the testing facility, or in one or more alternate or virtual locations, e.g., in a "cloud"-based environment. Moreover, the initial signature may be generated based at least in part on results of a modal analysis of the initial testing data captured by the aerial vehicle onboard sensors and testing facility sensors.

After initial testing of the aerial vehicle has been completed, and the initial signature has been generated thereby, the process advances to box 540, where the aerial vehicle departs for a mission, e.g., with a payload of one or more objects. At box 545, the aerial vehicle returns from the mission, e.g., after delivering a payload, or after retrieving a payload, and at box 550, the aerial vehicle is placed into a sensor-equipped testing facility upon its return. For example, the testing facility may be the same facility at which the initial testing was performed, or a similarly configured testing facility, which may be associated with a destination for the mission or, alternatively, an origin or an intermediate point that is neither the origin nor the destination.

At box 555, the aerial vehicle performs the automated testing sequence on the rotors and the control surfaces within the testing facility. In parallel, at boxes 560 and 565, the aerial vehicle's onboard sensors and the testing facility's ground-based sensors capture testing data during the performance of the automated testing sequence upon the return of the aerial vehicle. At box 570, the aerial vehicle uploads the testing data captured by the onboard sensors to the testing facility servers. Alternatively, the aerial vehicle may further upload environmental and/or operational data captured by the aerial vehicle during the mission, or any other relevant data regarding the aerial vehicle or the mission.

At box 575, a signature is generated based on the testing data captured by the aerial vehicle's onboard sensors and the testing facility's sensors. For example, where the initial signature was generated by providing the initial testing data to a machine learning system or tool, the testing data captured at box 560 and box 565 may also be provided to the same machine learning system or tool as inputs, and a signature may be generated based on outputs. The signature may be generated at box 575 based on the testing data in any manner consistent with the generation of the initial signature at box 535, e.g., based on a modal analysis of the testing data.

At box 580, whether the signature generated at box 575 is consistent with the initial signature generated at box 535 is determined. For example, where the initial signature generated at box 575 reflects sound pressure levels, frequency spectrums or other indicia of noise radiated by the aerial vehicle during initial testing, or vibrations experienced by the aerial vehicle during the initial testing, the signature generated at box 535 may be compared to the initial signature generated at box 575 to determine whether the sound pressure levels, frequency spectrums or other indicia of noise or vibration radiated by the aerial vehicle during testing or operation are consistent therewith, e.g., whether such indicia are equal to those of the initial signature, or within a predetermined range or limit thereof. The initial signature may also be defined for a class to which the aerial vehicle belongs, for the testing facility, for the mission, or on any other basis.

If the signature is consistent with the initial signature, then the process advances to box 585, where the aerial vehicle is cleared for additional missions, before returning to box 540, where the aerial vehicle departs for another mission. If the signature is not consistent with the initial signature, however, then the process advances to box 590, where the aerial vehicle is blocked from performing additional missions, and the process ends.

As is discussed above, the systems and methods of the present disclosure may determine whether an aerial vehicle is experiencing faults or discrepancies such as microfractures, cracks, loosened or broken fasteners, corrosions, fatigue, or evidence of other physical manifestations of stress or strain by capturing information and data regarding noise or vibrations radiating therefrom during the performance of an automated testing sequence using onboard sensors and/or ground-based sensors between phases of operation, such as upon returning from a first mission and prior to departing for a second mission. Such information or data may be compared to previously captured information or data regarding the performance of the automated testing sequence.

Figure 6A:
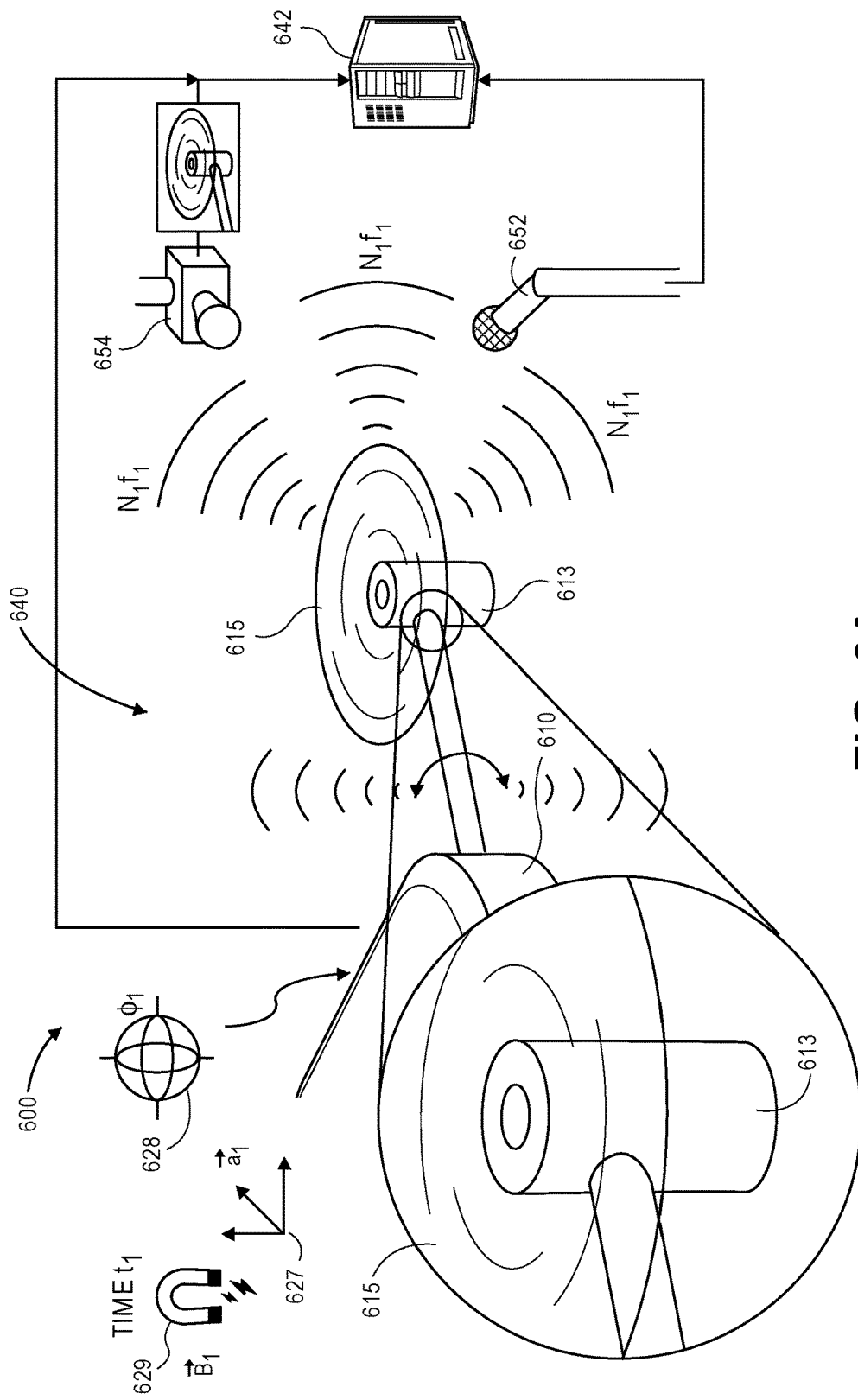
FIGS. 6A and 6B are views of aspects of one system for automated aerial vehicle inspections in accordance with embodiments of the present disclosure.
Figure 6B:
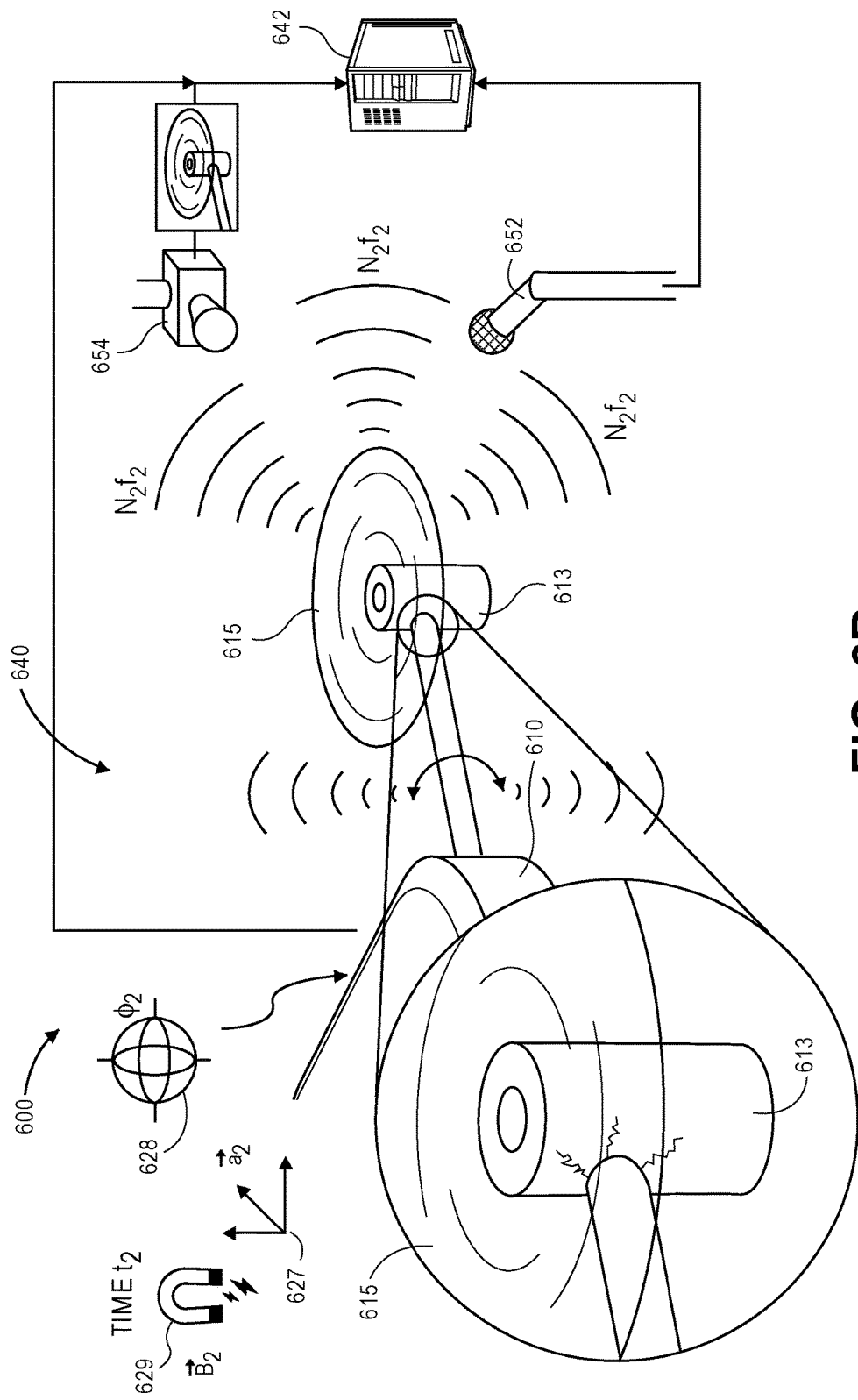

Referring to FIGS. 6A and 6B, views of aspects of one system 600 for automated aerial vehicle inspections in accordance with embodiments of the present disclosure are shown. Except where otherwise noted, reference numerals preceded by the number "6" shown in FIGS. 6A and 6B indicate components or features that are similar to components or features having reference numerals preceded by the number "4" shown in FIGS. 4A through 4C, by the number "2" shown in FIG. 2 or by the number "1" shown in FIGS. 1A through 1D.

The system 600 includes an aerial vehicle 610 and a testing facility 640. The aerial vehicle 610 includes at least one motor 613 having at least one rotor 615, as well as an accelerometer 627, a gyroscope 628 and a magnetometer 629. The testing facility 640 includes at least one server 642, at least one microphone 652 and at least one imaging device 654. As is shown in FIG. 6A, the aerial vehicle 610 may operate the motor 613 at a time $t_1$ to cause the rotor 615 to rotate in accordance with a predetermined testing sequence with one or more other motors and rotors (not shown) or control surfaces (not shown). The operation of the motor 613 and the rotor 615 may occur within an acoustic range of the microphone 652 and within a field of view of the imaging device 654.

During or following the operation of the motor 613, information regarding accelerations $a_1$ or orientations $\phi_1$ of the aerial vehicle 610 during the operation of the motor 613, or magnetic fields $B_1$ emitted by the aerial vehicle 610 during the operation of the motor 613, as determined by the accelerometer 627, the gyroscope 628 or the magnetometer 629, may be transferred from the aerial vehicle 610 to the testing facility servers 642. Likewise, acoustic data $N_1, f_1$ captured by the microphone 652 and imaging data captured by the imaging device 654 may also be transferred to the testing facility servers 642. A signature for the aerial vehicle 610 and/or the motor 613 operating at time $t_1$ may be generated by the testing facility servers 642 based on a modal analysis, or by any other algorithm or function, using the information or data captured by the accelerometer 627, the gyroscope 628, the magnetometer 629, the microphone 652 or the imaging device 654, or one or more other sensors (not shown) aboard the aerial vehicle 610 and/or at the testing facility 640. For example, the signature may indicate or reflect an extent to which the aerial vehicle 610 itself or one or more components thereof vibrates during an operation of the motor 613.

Similarly, the motor 613 may be operated again at a later time, according to an automated testing sequence executed upon an arrival during or after a mission, or between phases of operation of the aerial vehicle 610. As is shown in FIG. 6B, the aerial vehicle 610 may operate the motor 613 and the rotor 615 at a later time $t_2$, within the acoustic range of the microphone 652 and within the field of view of the imaging device 654. During or following the operation of the motor 613, information regarding accelerations $a_2$ or orientations $\phi_2$ of the aerial vehicle 610 during the operation of the motor 613, or magnetic fields $B_2$ emitted by the aerial vehicle 610 during the operation of the motor 613, as determined by the accelerometer 627, the gyroscope 628 or the magnetometer 629, as well as acoustic data $N_2$, $f_2$ captured by the microphone 652 and imaging data captured by the imaging device 654 may be transferred to the testing facility servers 642. A signature for the aerial vehicle 610 and/or the motor 613 operating at time $t_2$ may be generated by the testing facility servers 642 based on a modal analysis, or by any other algorithm or function, in the same manner as the signature for the aerial vehicle 610 and/or the motor 613 operating at time $t_1$. Differences between observed data as reflected in the respective signatures may indicate different levels of noise or vibration generated during the operation of the motor 613 at different times, suggesting that the motor 613 and/or one or more other components of the aerial vehicle 610 may require maintenance, repairs or further inspections.

Operating data or other information collected during the performance of a mission may be used to determine which or whether maintenance, repairs or inspections are to be performed upon a return of an aerial vehicle following the mission. The operating data may be transmitted to a testing facility or other facility for diagnoses or analyses, and, if necessary, one or more maintenance, repairs or inspections to be performed on the aerial vehicle (e.g., a customized testing sequence) may be recommended based on such diagnoses or analyses, either immediately or upon its return after completing the mission. If specific tests to be performed are not identified based on the diagnoses or analyses of the operating data, then the aerial vehicle may be subjected to a standard battery of tests (e.g., a standardized testing sequence) upon its return.

Figure 7:
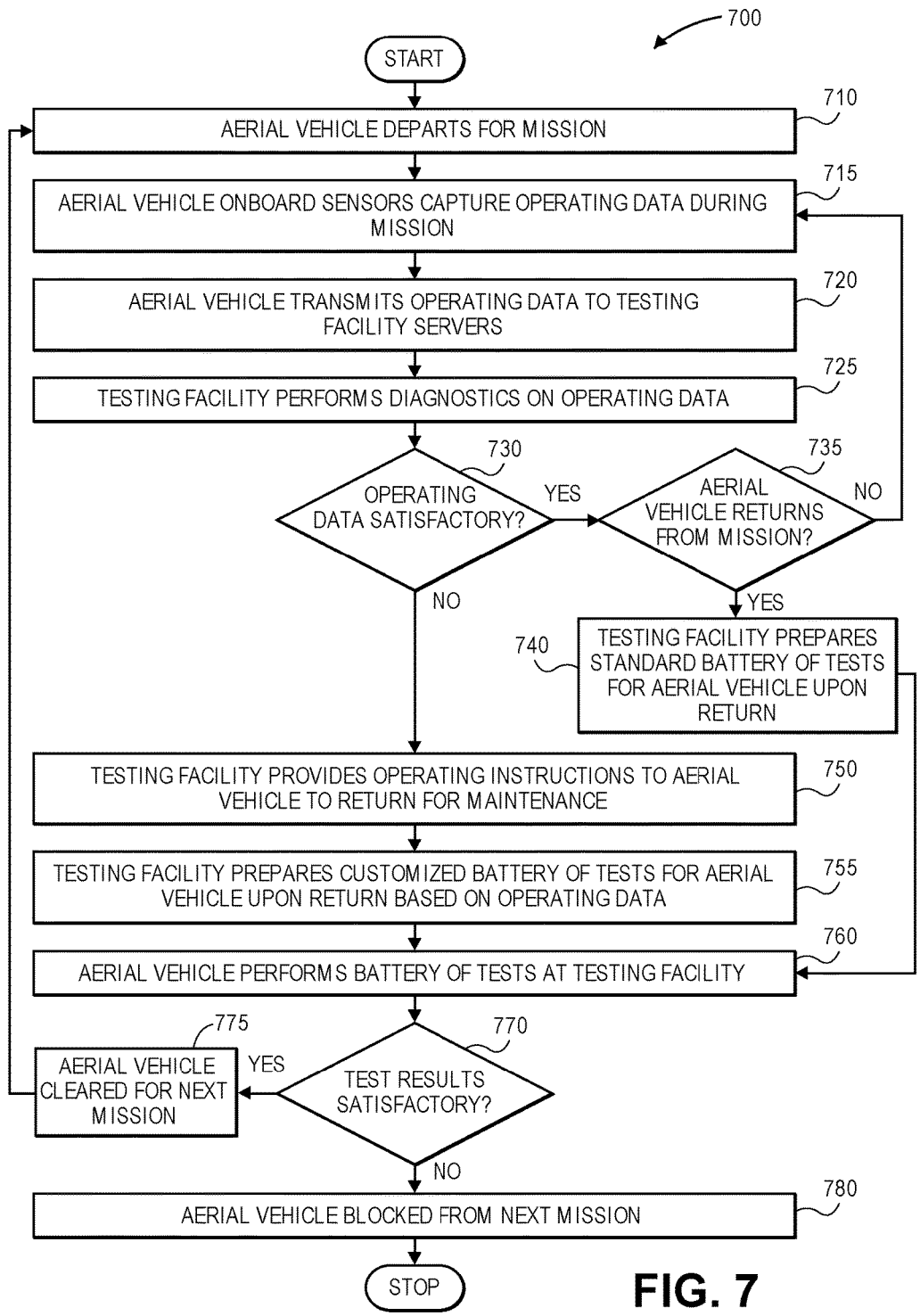
FIG. 7 is a flow chart of one process for automated aerial vehicle inspections in accordance with embodiments of the present disclosure.

Referring to FIG. 7, a flow chart 700 of one process for automated aerial vehicle inspections in accordance with embodiments of the present disclosure is shown. At box 710, an aerial vehicle departs for a mission, e.g., to deliver or retrieve a payload, and at box 715, sensors onboard the aerial vehicle capture operating data during the mission. For example, the operating data may relate to dynamic attributes such as altitudes, courses, speeds, rates of climb or descent, turn rates, or accelerations of the aerial vehicle during the mission, or noise or vibrations radiated thereby during the mission. Alternatively, information or data referring or relating to environmental conditions encountered during the mission (e.g., temperatures, pressures, humidities, wind speeds and directions), or any other relevant information or data regarding the mission, may also be captured.

At box 720, the aerial vehicle transmits the operating data to one or more testing facility servers. The transmission may occur wirelessly via one or more networks, such as cellular telephone networks, satellite networks, or the like, and may occur in real time (e.g., as the operating data is captured), in near-real time, or in one or more batch jobs, e.g., asynchronously or synchronously, or in accordance with a predetermined schedule or when the aerial vehicle is at a predetermined location, such as within a vicinity or range of a transmitting or receiving device (e.g., an antenna). At box 725, the testing facility performs one or more diagnostic operations on the operating data received from the aerial vehicle. For example, the testing facility may determine whether the aerial vehicle is operating normally, and in accordance with a transit plan, or whether the aerial vehicle has encountered one or more intrinsic or extrinsic faults or unexpected conditions, or is otherwise operating in an aberrant or erratic manner. At box 730, whether the operating data is satisfactory is determined, e.g., by comparison to one or more thresholds or ranges, or operating histories for the aerial vehicle in general, or for a specific environment in which the aerial vehicle is operating.

If the operating data is deemed satisfactory at box 730, then the process advances to box 735, where it is determined whether the aerial vehicle has returned from its mission. If the aerial vehicle has returned from its mission, then the process advances to box 740, where the process advances to box 740, where the testing facility prepares a standard battery of tests for the aerial vehicle, and to box 760, where the aerial vehicle performs the battery of tests at the testing facility. A standard battery of tests may include an automated testing sequence by which each of the motors, rotors and/or control surfaces of the aerial vehicle are operated independently or in tandem at the testing facility, e.g., within operating ranges of one or more ground-based sensors provided there. If the vehicle has not returned from its mission, then the process returns to box 715, where the aerial vehicle's onboard sensors continue to capture operating data during the mission.

If the operating data is deemed unsatisfactory at box 730, then the process advances to box 750, where the testing facility provides operating instructions to the aerial vehicle to return for maintenance. For example, the testing facility may instruct the aerial vehicle to return immediately to the testing facility (or to another location), without completing the mission or one or more portions thereof. Alternatively, the testing facility may instruct the aerial vehicle to return to the testing facility (or to another location) after completing the mission or portions thereof, e.g., under normal operating conditions, or under reduced or modified operating conditions, such as faster or slower speeds, higher or lower power levels and/or direct or modified courses. At box 755, the testing facility prepares a customized battery of tests for the aerial vehicle upon its return, based on the operating data.

At box 760, the aerial vehicle performs a battery of tests at the testing facility, e.g., either a standard battery of tests, as determined at box 740, or a customized battery of tests, as determined at box 760. The battery of tests may include a predetermined automated testing sequence in whole or in part, as well as one or more tests or evolutions that may be customized or selected for the aerial vehicle, for a class to which the aerial vehicle belongs, for the testing facility, or on any other basis. Additionally, as is discussed above, the battery of tests may be performed within an operating range (e.g., within an acoustic range and/or field of view) of one or more ground-based sensors provided at the testing facility. At box 770, whether the results of the battery of tests are satisfactory is determined. If the results of the tests are satisfactory, then the process advances to box 775, where the aerial vehicle is cleared for its next mission, and to box 710, where the aerial vehicle departs for that mission, e.g., to deliver or retrieve another payload. Alternatively, where the aerial vehicle was instructed to terminate its mission and return for testing at box 750, the aerial vehicle may resume the mission if the results of the tests are deemed satisfactory. If the results of the tests are unsatisfactory, however, then the process advances to box 780, where the aerial vehicle is blocked from performing its next mission, e.g., until further maintenance, repairs or further inspections are performed.

Those of ordinary skill in the pertinent art will recognize that the ground-based sensors (e.g., acoustic sensors, imaging devices or magnetometers) that are used to capture testing data from aerial vehicles during the performance of predetermined testing sequences may be provided about a landing area, e.g., at or near the landing pad 145 shown in FIGS. 1A through 1D, enabling a predetermined testing sequence to be performed when the aerial vehicle is on the ground. Alternatively, however, the ground-based sensors may be provided in a range or other alignment that enables testing data to be captured from aerial vehicles while the aerial vehicles are in flight.

Figure 8:
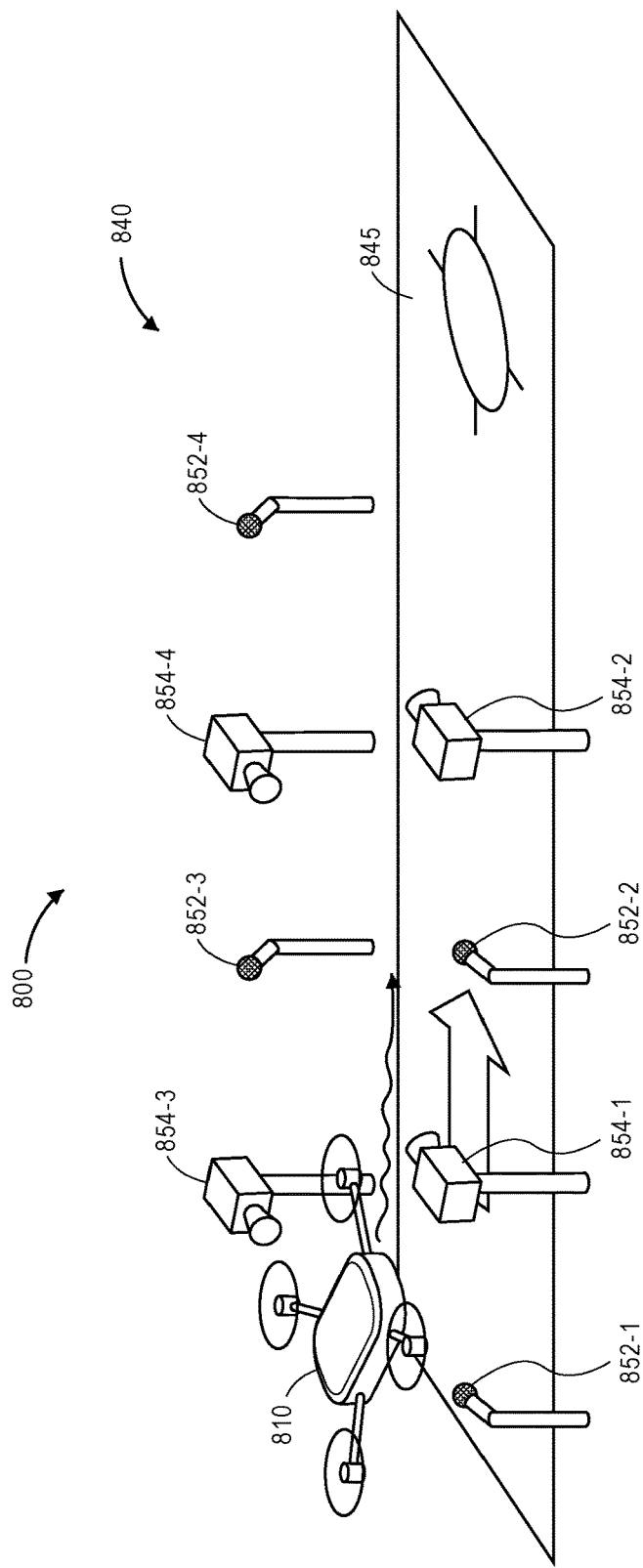
FIG. 8 is a view of aspects of one system for automated aerial vehicle inspections in accordance with embodiments of the present disclosure.

Referring to FIG. 8, a view of aspects of one system 800 for automated aerial vehicle inspections in accordance with embodiments of the present disclosure is shown. Except where otherwise noted, reference numerals preceded by the number "8" shown in FIG. 8 indicate components or features that are similar to components or features having reference numerals preceded by the number "6" shown in FIGS. 6A and 6B, by the number "4" shown in FIGS. 4A through 4C, by the number "2" shown in FIG. 2 or by the number "1" shown in FIGS. 1A through 1D.

As is shown in FIG. 8, the system 800 includes an aerial vehicle 810 and a testing facility 840. The testing facility 840 includes a plurality of acoustic sensors 852-1, 852-2, 852-3, 852-4 (e.g., microphones) and a plurality of imaging devices 854-1, 854-2, 854-3, 854-4 disposed on either side of a range 845. The aerial vehicle 810 is shown as passing over the range 845 as the aerial vehicle 810 returns to the testing facility 840, e.g., while completing a mission. Alternatively, the aerial vehicle 810 may pass over the range 845 as the aerial vehicle 810 departs from the testing facility, e.g., while beginning a mission. Testing data captured by the acoustic sensors 852-1, 852-2, 852-3, 852-4 and/or the plurality of imaging devices 854-1, 854-2, 854-3, 854-4 of the range 845 may be evaluated to determine whether the aerial vehicle 810 requires any maintenance, repairs or further inspections, or whether the aerial vehicle 810 may be cleared for its next mission.

Those of ordinary skill in the pertinent arts will recognize that the aerial vehicle 810 may operate in any number of modes while passing over or near the acoustic sensors 852-1, 852-2, 852-3, 852-4 and the imaging devices 854-1, 854-2, 854-3, 854-4 of the range 845, e.g., including but not limited to a predetermined testing sequence by which one or more motors, rotors or control surfaces provided on the aerial vehicle are operated at different powers or subject to different limits. Moreover, those of ordinary skill in the pertinent arts will recognize that in addition to testing data captured by the acoustic sensors 852-1, 852-2, 852-3, 852-4 and the imaging devices 854-1, 854-2, 854-3, 854-4 of the range 845, testing data captured by one or more sensors onboard the aerial vehicle 810 may also be used to determine whether the aerial vehicle 810 requires any maintenance, repairs or further inspections, or whether the aerial vehicle 810 may be cleared for its next mission.

Ground-based sensors from which testing data may be captured may be stationary or in motion. For example, a testing facility may include a plurality of landing areas or other spaces at which aerial vehicles may be subjected to one or more testing evolutions, and a sensor provided on a vehicle or robot (e.g., a cart, a truck, a mobile platform or other machine) configured to travel on a road, a path, a track, or one or more rails may be used to capture information or data regarding aerial vehicles that are located at the different landing areas or other spaces. The ability of a sensor to travel from one landing area or other space to another landing area or another space, and to evaluate multiple aerial vehicles in such areas or spaces, may be particularly useful where the sensor is unique or expensive, e.g., a high frame rate camera or high fidelity acoustic sensor, or any other type or form of sensor.

Figure 9A:
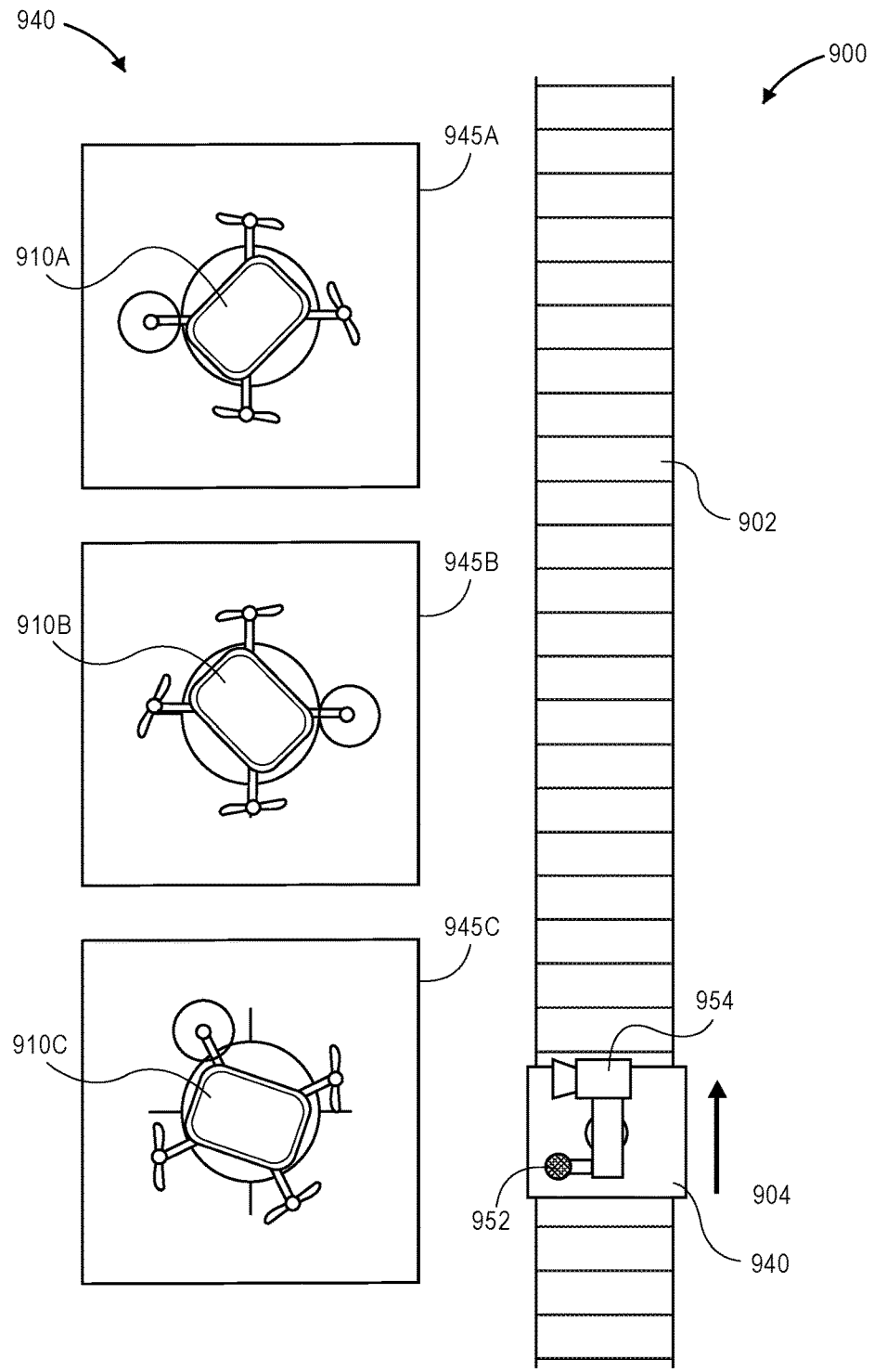
FIGS. 9A and 9B are views of aspects of one system for automated aerial vehicle inspections in accordance with embodiments of the present disclosure.
Figure 9B:
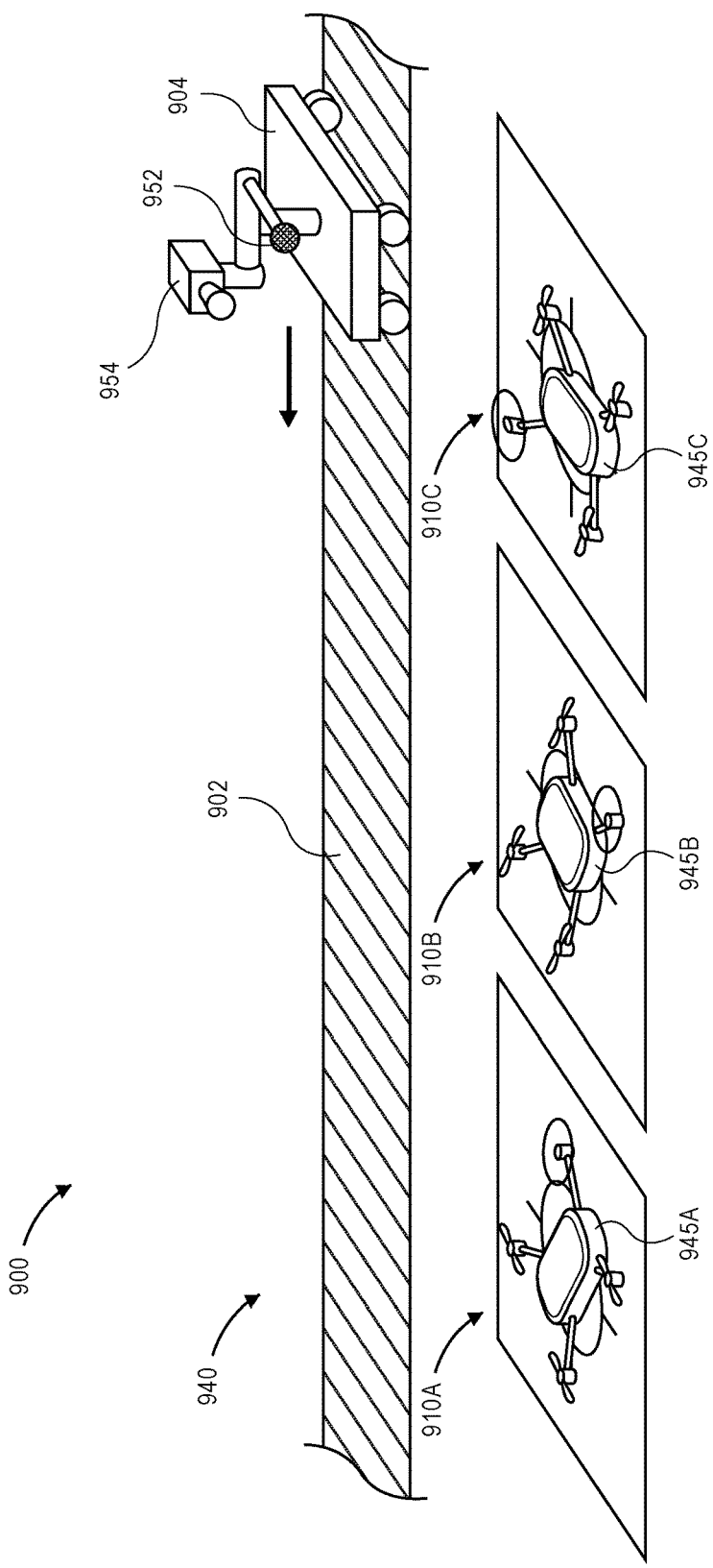

Referring to FIGS. 9A and 9B, views of aspects of one system 900 for automated aerial vehicle inspections in accordance with embodiments of the present disclosure is shown. Except where otherwise noted, reference numerals preceded by the number "9" shown in FIGS. 9A and 9B indicate components or features that are similar to components or features having reference numerals preceded by the number "8" shown in FIG. 8, by the number "6" shown in FIGS. 6A and 6B, by the number "4" shown in FIGS. 4A through 4C, by the number "2" shown in FIG. 2 or by the number "1" shown in FIGS. 1A through 1D.

As is shown in FIGS. 9A and 9B, the system 900 includes a testing facility 940 having a track 902 and a plurality of landing areas 945A, 945B, 945C. The track 902 may include one or more rails that are sized or configured for a vehicle 904 to travel thereon. The vehicle 904 includes an acoustic sensor 952 (e.g., a microphone) and an imaging device 954 (e.g., a digital camera), and may include one or more other sensors (not shown). The landing areas 945A, 945B, 945C each include an aerial vehicle 910A, 910B, 910C thereon. The track 902 is aligned to permit the vehicle 904 to pass by the respective landing areas 945A, 945B, 945C within operating ranges of the sensors thereon, e.g., within an acoustic range of the acoustic sensor 952 or within a field of view of the imaging device 954. Thus, each of the aerial vehicles 910A, 910B, 910C may be subjected to one or more testing evolutions (or sequences of such evolutions), and information or data regarding the aerial vehicles 910A, 910B, 910C may be captured using the acoustic sensor 952, the imaging device 954, or any other sensors provided at the testing facility 940 or aboard the respective vehicles 910A, 910B, 910C (not shown). Thus, a single sensor provided on a vehicle, or a set or complement of sensors provided on a vehicle, may be used to capture data during the performance of any number of testing evolutions by aerial vehicles that have returned from completing a mission, or are between phases of operation. Although the vehicle 904 is shown as configured for travel on the track 902 (e.g., on rails) and as including the acoustic sensor 952 and the imaging device 954, those of ordinary skill in the pertinent arts will recognize that any number of sensors, of any type, may be provided on any type of vehicle in accordance with the present disclosure.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

For example, although some of the embodiments disclosed herein reference the use of unmanned aerial vehicles to deliver payloads from warehouses or other like facilities to customers, those of ordinary skill in the pertinent arts will recognize that the systems and methods disclosed herein are not so limited, and may be utilized in connection with any type or form of aerial vehicle (e.g., manned or unmanned) having fixed or rotating wings for any intended industrial, commercial, recreational or other use.

It should be understood that, unless otherwise explicitly or implicitly indicated herein, any of the features, characteristics, alternatives or modifications described regarding a particular embodiment herein may also be applied, used, or incorporated with any other embodiment described herein, and that the drawings and detailed description of the present disclosure are intended to cover all modifications, equivalents and alternatives to the various embodiments as defined by the appended claims. Moreover, with respect to the one or more methods or processes of the present disclosure described herein, including but not limited to the processes represented in the flow charts of FIGS. 3, 5A and 5B, or 7, orders in which such methods or processes are presented are not intended to be construed as any limitation on the claimed inventions, and any number of the method or process steps or boxes described herein can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain embodiments could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative embodiments thereof, the foregoing and various other additions and omissions may be made therein and thereto without departing from the spirit and scope of the present disclosure.

What is claimed is:

1. A method to inspect a first aerial vehicle comprising a plurality of powered elements, the method comprising:
   initiating a first operation of a first powered element of the first aerial vehicle within a first portion of a testing facility, wherein the testing facility comprises a first sensor, and wherein the first portion of the testing facility is within a first operating range of the first sensor;
   during the first operation, capturing first data regarding the first operation of the first powered element by at least the first sensor;
   initiating a second operation of a second powered element of the first aerial vehicle within the first portion of the testing facility;
   during the second operation, capturing second data regarding the second operation of the second powered element by at least the first sensor;
   determining, by at least one computer processor, whether the first aerial vehicle requires at least one maintenance evolution based at least in part on the first data and the second data;
   in response to determining that the first aerial vehicle requires the at least one maintenance evolution,
      performing the at least one maintenance evolution on the first aerial vehicle.

2. The method of claim 1, further comprising:
   in response to determining that the first aerial vehicle does not require the at least one maintenance evolution,
      causing the first aerial vehicle to perform at least a first mission.

3. The method of claim 1, wherein the testing facility further comprises a second sensor,
   wherein the first portion of the testing facility is within a second operating range of the second sensor, and
   wherein the method further comprises:
   during the first operation, capturing third data regarding the first operation of the first powered element by at least the second sensor; and
   during the second operation, capturing fourth data regarding the second operation of the second powered element by at least the second sensor,
   wherein whether the first aerial vehicle requires the at least one maintenance evolution is determined based at least in part on the first data, the second data, the third data and the fourth data.

4. The method of claim 3, wherein the first sensor comprises at least one of a first imaging device, a first acoustic sensor, or a first magnetometer, and
   wherein the second sensor comprises at least one of a second imaging device, a second acoustic sensor, or a second magnetometer.

5. The method of claim 3, wherein determining whether the first aerial vehicle requires at least one maintenance evolution comprises:
   performing a first modal analysis regarding the first powered element based at least in part on at least the first data and the third data;
   generating a first signature for the first powered element based at least in part on the first modal analysis; and
   determining a comparison of the first signature to a second signature for the first powered element,
   wherein whether the first aerial vehicle requires the at least one maintenance evolution is determined based at least in part on the comparison of the first signature to the second signature.

6. The method of claim 5, further comprising:
   initiating a third operation of the first powered element of the first aerial vehicle within the first portion of the testing facility;
   during the third operation, capturing fifth data regarding the third operation of the first powered element by at least the first sensor;
   during the third operation, capturing sixth data regarding the third operation of the first powered element by at least the second sensor;
   performing a second modal analysis regarding the first powered element based at least in part on at least the fifth data and the sixth data;

generating the second signature for the first powered element based at least in part on the second modal analysis,
wherein the third operation of the first powered element precedes the first operation of the first powered element.

7. The method of claim 5, wherein determining the comparison of the first signature to the second signature further comprises:
providing at least the first signature and the second signature as inputs to a machine learning algorithm; and
receiving an output from the machine learning algorithm, wherein whether the first aerial vehicle requires the at least one maintenance evolution is determined based at least in part on the output received from the machine learning algorithm.

8. The method of claim 1, wherein the first aerial vehicle further comprises a second sensor, and
wherein the method further comprises:
during the first operation, capturing third data regarding the first operation of the first powered element by at least the second sensor; and
during the second operation, capturing fourth data regarding the second operation of the second powered element by at least the second sensor,
wherein whether the first aerial vehicle requires the at least one maintenance evolution is determined based at least in part on the first data, the second data, the third data and the fourth data.

9. The method of claim 8, wherein the second sensor comprises at least one of a gyroscope, an accelerometer, a magnetometer, an imaging device, or an acoustic sensor.

10. The method of claim 1, wherein the first powered element comprises at least one of a first motor coupled to a first rotor or a first control surface, and
wherein the second powered element comprises at least one of a second motor coupled to a second rotor or a second control surface.

11. The method of claim 1, further comprising:
identifying a testing sequence associated with the first aerial vehicle, wherein the testing sequence comprises operating each of the plurality of powered elements of the first aerial vehicle,
wherein the first operation and the second operation are initiated in accordance with an execution of the testing sequence.

12. The method of claim 1, further comprising:
in response to determining that the first aerial vehicle does not require the at least one maintenance evolution, causing the first aerial vehicle to perform at least a first mission;
identifying a testing sequence associated with the first aerial vehicle, wherein the testing sequence comprises an operation of each of the plurality of powered elements of the first aerial vehicle, wherein the first operation and the second operation are initiated in accordance with a first execution of the testing sequence;
receiving the first aerial vehicle within the first portion of the testing facility after the performance of at least the first mission; and
initiating a second execution of the testing sequence after the performance of at least the first mission, wherein initiating the second execution of the testing sequence further comprises:
initiating a third operation of the first powered element of the first aerial vehicle within the first portion of the testing facility;
during the third operation, capturing third data regarding the third operation of the first powered element by at least the first sensor;
initiating a fourth operation of the second powered element of the first aerial vehicle within the first portion of the testing facility;
during the fourth operation, capturing fourth data regarding the fourth operation of the second powered element by at least a second sensor; and
determining, by at least one computer processor, whether the first aerial vehicle requires at least one maintenance evolution following at least the first mission based at least in part on the third data and the fourth data; and
in response to determining that the first aerial vehicle requires the at least one maintenance evolution following at least the first mission,
performing the at least one maintenance evolution on the first aerial vehicle following at least the second execution of the testing sequence.

13. The method of claim 1, wherein the first data comprises at least one of:
an acceleration of at least a portion of the aerial vehicle during the first operation;
a vibration frequency of at least the portion of the aerial vehicle during the first operation;
imaging data captured during the first operation;
acoustic data captured during the first operation; and
a magnetic field emitted by the aerial vehicle during the first operation.

14. The method of claim 1, further comprising:
receiving operational data regarding at least a second mission performed by the first aerial vehicle,
wherein the second mission preceded the first mission,
wherein the operational data comprises at least one of a speed of the first aerial vehicle during the second mission, a course of the first aerial vehicle during the second mission, an altitude of the first aerial vehicle during the second mission, an origin of the first aerial vehicle during the second mission or a destination of the first aerial vehicle during the second mission, and
wherein whether the first aerial vehicle requires the at least one maintenance evolution is determined based at least in part on the operational data.

15. The method of claim 1, wherein the at least one maintenance evolution is at least one of a repair of at least one of the first powered element or the second powered element, or
an inspection of the at least one of the first powered element or the second powered element for at least one of a microfracture, a crack, a loosened fastener, a broken fastener, corrosion or fatigue.

16. The method of claim 1, wherein the first portion of the testing facility comprises at least one of a landing area or a range associated with the testing facility.

17. The method of claim 1, wherein the testing facility further comprises a vehicle,
wherein the first sensor is mounted to the vehicle, and
wherein the vehicle is configured to place the first sensor within the first operational range of the first portion of the testing facility and within a second operational range of a second portion of the testing facility having a second aerial vehicle therein.

18. A method comprising:
receiving operating data from an aerial vehicle over a network, wherein the aerial vehicle comprises a powered motor and a pivotable control surface, and wherein the operating data comprises at least one of a speed, a course, an altitude or a radiated noise level during a mission;
providing information to the aerial vehicle in response to receiving the operating data, wherein the information includes an instruction to travel to a location of a testing facility;
determining that the aerial vehicle has arrived at a landing area of the testing facility, wherein the landing area is within an operating range of at least a first sensor;
causing a first operation of the powered motor at a predetermined operating speed;
during the first operation, capturing first data using at least the first sensor;
determining whether the first data is consistent with at least one physical manifestation of stress or strain associated with the powered motor; and
in response to determining that the first data is consistent with the at least one physical manifestation of stress or strain associated with the powered motor,
storing, in at least one data store, an indication that a visual inspection of at least the powered motor is required.

19. The method of claim 18, further comprising:
after the first operation,
causing a second operation of the pivotable control surface within a predetermined angular range;
during the second operation, capturing second data using at least the first sensor;
determining whether the second data is consistent with at least one physical manifestation of stress or strain associated with the pivotable control surface; and
in response to determining that the second data is consistent with at least one physical manifestation of stress or strain associated with the pivotable control surface,
storing, in at least one data store, an indication that a visual inspection of at least the pivotable control surface is required.

20. The method of claim 19, further comprising:
selecting a testing sequence for the aerial vehicle based at least in part on the operating data; and
executing the testing sequence on the aerial vehicle in response to determining that the aerial vehicle has arrived at the landing area of the testing facility,
wherein the testing sequence comprises:
causing the first operation of the powered motor at the predetermined operating speed; and
causing the second operation of the pivotable control surface within the predetermined angular range after the first operation.

21. A system comprising:
a testing facility having at least a landing area, an imaging device, a first microphone and a first computing device connected to a network, wherein at least a portion of the landing area is within a field of view of the imaging device, and wherein at least the portion of the landing area is within an acoustic range of the first microphone; and
an aerial vehicle having at least a first rotor coupled to a first motor, a second rotor coupled to a second motor, a second microphone and a second computer device connected to the network, wherein the aerial vehicle is within the portion of the landing area,
wherein the first computing device is configured to at least:
receive, from the second computing device over the network, first information regarding a first mission previously executed by the aerial vehicle, wherein at least some of the first information was captured by the second microphone during the first mission;
cause a first operation of the first motor at a first speed;
during the first operation,
cause the imaging device to capture first imaging data of at least the first motor or the first rotor; and
cause the first microphone to capture first acoustic data;
cause a second operation of the second motor at a second speed;
during the second operation,
cause the imaging device to capture second imaging data of at least the second motor or the second rotor; and
cause the first microphone to capture second acoustic data;
receive, from the imaging device, the first imaging data and the second imaging data;
receive, from the first microphone, the first acoustic data and the second acoustic data;
identify a first signature associated with operation of at least one of the first motor or the second motor;
generate a second signature based at least in part on at least one of the first information regarding the first mission, the first imaging data, the second imaging data, the first acoustic data or the second acoustic data;
determine whether the second signature is consistent with the first signature; and
upon determining that the second signature is not consistent with the first signature,
identify a discrepancy between the second signature and the first signature;
determine a maintenance evolution associated with the discrepancy; and
block the aerial vehicle from performing a second mission until the maintenance evolution is completed.

22. The system of claim 21, wherein the first computing device is further configured to at least:
upon determining that the second signature is consistent with the first signature,
clear the aerial vehicle to perform the second mission.

23. The system of claim 21, wherein the first computing device is further configured to at least:
identify a testing sequence for the aerial vehicle, wherein the testing sequence comprises operating the first motor and the second motor in series,
wherein the first computing device is configured to cause the first operation of the first motor and the second operation of the second motor in accordance with the testing sequence,
wherein the first signature was generated based at least in part on third imaging data captured during a third operation of the first motor in accordance with the testing sequence, fourth imaging data captured during a fourth operation of the second motor in accordance with the testing sequence, third acoustic data captured during the third operation and fourth acoustic data captured by the fourth operation, and
wherein the third operation and the fourth operation preceded the first mission.

24. The system of claim 23, wherein the aerial vehicle further comprises a control surface,
  wherein the testing sequence further comprises operating the control surface, and
  wherein the first computing device is further configured to at least:
    cause a fifth operation of the control surface in accordance with the testing sequence;
    during the fifth operation,
      cause the imaging device to capture fifth imaging data of at least the control surface; and
      cause the first microphone to capture fifth acoustic data; and
    generate the second signature based at least in part on the fifth imaging data and the fifth acoustic data,
    wherein the first signature was generated based at least in part on sixth imaging data captured during a sixth operation of the control surface in accordance with the testing sequence and sixth acoustic data captured during the sixth operation, and
    wherein the sixth operation preceded the first mission.

25. The system of claim 23, wherein the first computing device is further configured to at least:
  perform a first modal analysis on at least one of the third imaging data, the fourth imaging data, the third acoustic data and the fourth acoustic data;
  generate the first signature based at least in part on the first modal analysis;
  perform a second modal analysis on at least one of the first information regarding the first mission, the first imaging data, the second imaging data, the first acoustic data and the second acoustic data; and
  generate the second signature based at least in part on the second modal analysis.

* * * * *

UNITED STATES PATENT AND TRADEMARK OFFICE
CERTIFICATE OF CORRECTION

PATENT NO.         : 10,053,236 B1
APPLICATION NO.    : 15/083161
DATED              : August 21, 2018
INVENTOR(S)        : Daniel Buchmueller and Samuel Sperindeo It is certified that error appears in the above-identified patent and that said Letters Patent is hereby corrected as shown below:

On the Title Page

Item (56)

References Cited

Page 2, Column 2, OTHER PUBLICATIONS Line 30 should be added as shown:
K. He, X. Zhang, S. Ren, and J. Sun. Deep Residual Learning for Image Recognition. In Proceedings of the IEEE Conference on Computer Vision and Pattern Recognition (CVPR 2016), Las Vegas, Nevada, pages 770–778, IEEE 2016.

Page 2, Column 2, OTHER PUBLICATIONS Line 30 delete:
"D. Mery and M.A. Berti. Automatic Detection of Welding Defects Using Texture Features. Insight-Non- Destructive Testing and Condition Monitoring, 45(10):676–681, 2003. Presented at Int'l Symposium on Computed Tomography and Image Processing for Industrial Radiology, Berlin, Germany, June 23-25, 2003."

Signed and Sealed this
Thirteenth Day of February, 2024

Katherine Kelly Vidal
*Director of the United States Patent and Trademark Office*